United States Patent
Chung et al.

(10) Patent No.: US 7,589,072 B2
(45) Date of Patent: Sep. 15, 2009

(54) INOSITOL-BASED MOLECULAR TRANSPORTERS AND PROCESSES FOR THE PREPARATION THEREOF

(75) Inventors: Sung-Kee Chung, Pohang-si (KR);
Ock-Younm Jeon, Seongnam-si (KR);
Kaustabh Kumar Maiti, Pohang-si (KR); Seok-Ho Yu, Pohang-si (KR)

(73) Assignee: Postech Foundation, Pohang-si (KR)

( * ) Notice: Subject to any disclaimer, the term of this patent is extended or adjusted under 35 U.S.C. 154(b) by 215 days.

(21) Appl. No.: 10/565,164

(22) PCT Filed: Aug. 6, 2004

(86) PCT No.: PCT/KR2004/001982

§ 371 (c)(1),
(2), (4) Date: Jan. 19, 2006

(87) PCT Pub. No.: WO2005/085159

PCT Pub. Date: Sep. 15, 2005

(65) Prior Publication Data
US 2006/0280796 A1    Dec. 14, 2006

(30) Foreign Application Priority Data
Mar. 5, 2004    (KR) ............ 10-2004-0014833

(51) Int. Cl.
*A01N 43/04* (2006.01)
*A61K 31/70* (2006.01)
*A61K 9/127* (2006.01)
*C07C 69/34* (2006.01)
*C07C 69/52* (2006.01)
*C07C 233/00* (2006.01)
*C07C 235/00* (2006.01)
*C07C 237/00* (2006.01)
*C07C 239/00* (2006.01)

(52) U.S. Cl. .................. 514/44; 424/450; 560/198; 564/123

(58) Field of Classification Search ............ None
See application file for complete search history.

(56) References Cited

U.S. PATENT DOCUMENTS 6,187,335 B1    2/2001    Brey et al.
6,495,663 B1    12/2002    Rothbard et al.

FOREIGN PATENT DOCUMENTS

WO    WO 0265986 A2 *    8/2002

OTHER PUBLICATIONS

Lundberg, et al. (2003) Molecular Therapy, 8(1): 143-150.*
Rothbard, et al. (2002) Journal of Medicinal Chemistry, 45(17): 3612-18.*
Tomera, et al. (1993) J. Burn. Care. Rehabil., 14(6): 639-52, Abstract Only.*

* cited by examiner

*Primary Examiner*—Robert M Kelly
(74) *Attorney, Agent, or Firm*—Sughrue Mion, PLLC

(57) ABSTRACT

Inositol derivatives in accordance with the present invention are effective in significantly enhancing the transportation of various therapeutic molecules across a biological membrane, which may include the plasma membrane, nuclear membrane or blood-brain barrier.

12 Claims, 2 Drawing Sheets
(2 of 2 Drawing Sheet(s) Filed in Color)

INOSITOL-BASED MOLECULAR TRANSPORTERS AND PROCESSES FOR THE PREPARATION THEREOF

FIELD OF THE INVENTION

The present invention relates to inositol-based molecular transporters and processes for the preparation thereof.

BACKGROUND OF THE INVENTION

The plasma membrane of a cell separates the cytoplasm of the cell from the environment, and it is primarily composed of a phospholipid bilayer and proteins embedded within the bilayer or attached to the surface thereof. Normally the plasma membrane functions as a gate-keeper which allows essential substances to enter and exit the cell. However, the cell plasma membrane is a selective permeability barrier which blocks the passage of many useful therapeutic agents: hydrophilic molecules, highly charged molecules and macromolecules such as peptides and oligonucleotides, e.g., nucleic acid or gene, cannot be transported across the plasma membrane. Therefore, there has been a need for a reliable means of transporting drugs and macromolecules into cells.

Heretofore, a number of transporter molecules have been proposed to escort molecules across biological membranes. The proposed transporter molecules are lipids having positively charged residues, polymers of positively charged residues such as poly-lysine, and dendrimers having positively charged residues. However, such lipids, polymers and dendrimers have a common problem in that they are not easily soluble or biodegradable, and hence, precipitate in a cell to induce toxicity.

The basic region (i.e., AA 49-57) of Tat protein, which is a necessary trans-activator of HIV virus reproduction, has been reported to play a critical role in the process of the protein permeation through the plasma membrane. Proteins having a PTD (i.e., protein transduction domain) like the Tat basic region, that allows permeation through the plasma membrane include Antennapedia (Antp) homeodomain protein, Herpes virus protein VP22, Nuclear localization signal (NLS) sequence and the like, as shown in Table 1.

TABLE 1

| Protein having PTD | Amino acid sequence | SEQ ID NO: |
|---|---|---|
| HIV-1 Tat (48-60) | GRKKRRQRRRPPQ | 1 |
| Antp (43-58) | RQIKIWFQNRRMKWKK | 2 |
| VP22 (267-300) | DAATATRGRSAASRPTERDRAPARSASRPRRPVE | 3 |
| SV40-NLS | PKKKRKVC | 4 |
| Nucleo-plasmin | KRPAAIKKAGQAKKKKC | 5 |
| NF-kB | PMLKQRKRQA | 6 |
| HIV-1 Rev (34-50) | RQARRNRRRRWRERQRG | 7 |
| FHV Coat (35-49) | RRRNRTRRNRRRVRRGC | 8 |

The above proteins seem to be capable of permeating across biological membranes without help of any specific receptor or transporter associated with the cell. Further, they share a common feature in that they mainly consist of basic amino acids, especially arginine and lysine.

Various hypotheses have been proposed with regard to the transmembrane mechanism of these proteins. One of the most plausible among them is that such proteins having a PTD can be transported into a cell by endocytosis-like process. Lebleu et al. (2003) determined using fluorescence activated cell sorter (FACS) that HIV-1 Tat (AA 48-60) and arginine nonamer ($Arg_9$) are transported into a cell by endocytosis. However, the basic mechanism thereof has not yet been elucidated (Lebleu, B. et al., *Biol. Chem.*, 278, 585, (2003)).

Further, there have been reported various studies to prepare oligomers having a plurality of arginine residues so as to have a high permeability into a cell. For example, Mann et al. (1991) showed that Tat protein is effective in enhancing the transportation of molecules attached thereto across a biological membrane. However, he also reported the problem that the total number of Tat proteins actually delivered into a cell is limited, because they are water-insoluble and too strongly bound to the cell surface, which leads to agglomeration among themselves (Mann, D. A. et al., *EMBO J.*, 10, 1733 (1991)).

Barsoum et al. (1994) showed that shorter fragments of Tat protein (AA 1-72) and other fragments of the Tat protein containing the Tat basic region (AA 37-58) are also effective in enhancing the transportation of molecules attached thereto across a biological membrane. This study has shown that small peptides composed of amino acid residues contribute to the enhanced transportation of the molecules attached thereto across a biological membrane (Barsoum, J. et al., *Proc. Natl. Acad. Sci. U.S.A.*, 91, 664(1994)).

Futaki et al. (2001) examined membrane permeabilities into mouse macrophage RAW264.7 cell of various peptides having a plurality of arginine residues by way of attaching thereto a fluorescent tag. The result revealed that a peptide having many arginine residues shows a permeability similar to that of Tat protein (AA 49-57), and an oligomer having eight (8) arginine residues is most effective in enhancing the transportation of molecules attached thereto across a biological membrane (Futaki, S. et al., *J. Biol. Chem.*, 276, 5836 (2001)). These studies suggest that the guanidinium group of arginine is essential in the transportation of molecules attached thereto across a biological membrane.

Wender et al. (2000) designed a peptoid molecular transporter based on the fact that the biological membrane permeability depends on the number of the guanidinium group in a peptide, the length of the linker chain and chirality etc. Specifically, he noted that an L-arginine nonamer is 20-times more effective in the transportation across a biological membrane than Tat protein (AA 49-57), and a D-arginine nonamer is also significantly more effective in the transportation into a Jurkat cell, as was determined using FACS. Accordingly, the permeability of a peptoid having guanidinium groups is not significantly affected by the chirality of the amino acid (U.S. Pat. No. 6,495,663 and Wender, P. A. et al., *Proc. Natl. Acad. Sci. U.S.A.*, 97, 13003 (2000)). However, such polyarginine peptide or peptoid molecules have the problems of rapid metabolism and elimination through the liver and kidney as well as their in vivo toxicity liability.

The present invention is based on the finding that inositol derivatives prepared from myo-inositol and a plurality of positively charged guanidinium groups significantly enhances the transportation of various therapeutic molecules attached thereto across a biological membrane.

SUMMARY OF THE INVENTION

It is the objective of the present invention to provide inositol-based molecular transporters, which are effective in the transportation of therapeutic molecules across a biological membrane and processes for the preparation thereof.

It is another objective of the present invention to provide a composition for delivering a therapeutic molecule into a cell, comprising the inositol-based transporter.

BRIEF DESCRIPTION OF THE DRAWINGS

The patent or application file contains at least one drawing executed in color. Copies of this patent or patent application publication with color drawing(s) will be provided by the Office upon request payment of the necessary fee.

The above and other objectives and features of the present invention will become apparent from the following description of the invention, when taken in conjunction with the accompanying drawings, in which.

DETAILED DESCRIPTION OF THE INVENTION

Figure 1:
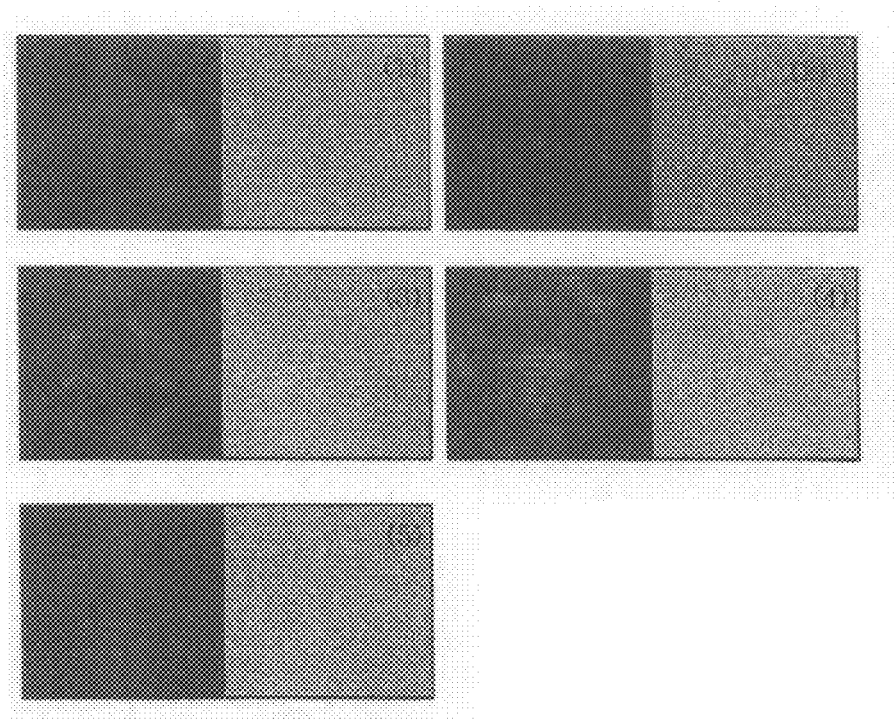
FIG. 1 shows comparative degrees of plasma membrane transmission of various compounds, dansyl-$Arg_9$ (1), the intermediate prepared in Example 1-6) having no guanidinium group (2), and the inositol derivatives in accordance with Examples 1 and 2 of the present invention (3 to 5)

In accordance with one aspect of the present invention, there is provided an inositol derivative of formula (I):

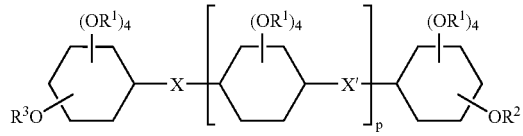

(I)

wherein
$R^1$ is

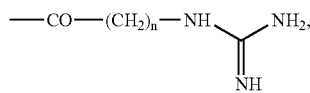

where n is an integer in the range of 1 to 12;
$R^2$ and $R^3$ are each independently H, alkyl, arylalkyl, cycloalkyl, heteroalkyl, —$(CH_2)_m$NHR', —$(CH_2)_l$$CO_2$R", —COR''' or —$SO_2$R'''', where R', R", R''' and R'''' are each alkyl, m is an integer in the range of 2 to 5, and l is an integer in the range of 1 to 5;
p is an integer in the range of 0 to 2; and
X and X' are each independently —O—CO—O—, —O—CO—NH—$(CH_2)_m$—O—, —O—CO—$(CH_2)_l$—O— or —O—$(CH_2)_l$—CO—NH—$(CH_2)_m$—O—, where m and l are the same as defined above.

In accordance with another aspect of the present invention, there is provided a method for preparing the inositol derivatives of formula (I), comprising the steps of:
(a) obtaining intermediates by protecting the hydroxyl groups of myo- or scyllo-inositol;
(b) obtaining inositol polymers by coupling two or more of the intermediates obtained in step (a);
(c) introducing one or more amino acids to the inositol polymer obtained in step (b) by acylation; and
(d) introducing guanidinium groups to the amino acid N-terminal of the inositol polymer.

The inositol derivative of formula (I) according to the present invention has an inositol skeleton having multiple guanidine groups in the side chains, which may exist as various isomers depending on the substitution pattern. Further, the inventive inositol derivative of formula (I) can be an inositol dimer (p=0), an inositol trimer (p=1) or an inositol tetramer (p=2), the inositol dimer and trimer being more preferred.

In a preferred embodiment of the invention, n is an integer in the range of 3 to 8. Such a compound having said n value shows an improved efficacy in the molecular transportation across a biological membrane.

A preferred inositol derivative according to the present invention is represented by formula (XV):

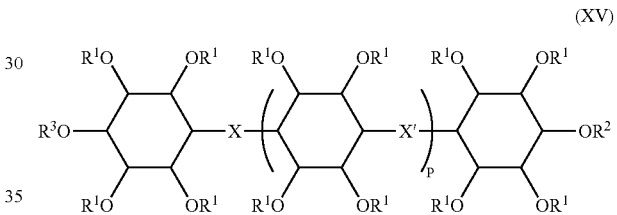

(XV)

wherein $R^1$, $R^2$, $R^3$, X, X' and p are the same as defined above.

A preferred inositol dimer of the type (p=0) of formula (I) is represented by formulae (II) to (IV):

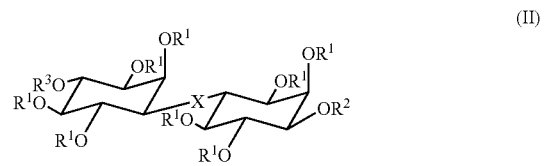

(II)

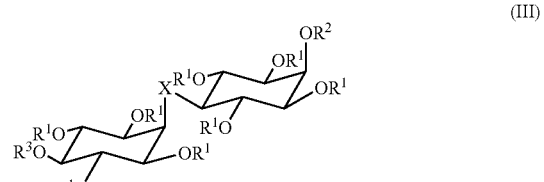

(III)

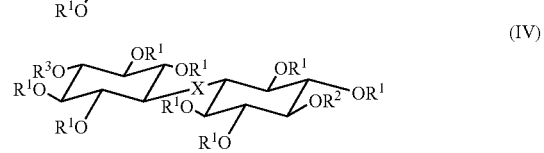

(IV)

wherein $R^1$, $R^2$, $R^3$ and X are the same as defined above.

The substituents $R^2$ and $R^3$ of the inositol derivatives of formulae (II) to (IV) may be therapeutic molecules such as drugs and diagnostic reagents, which can be attached to the inositol derivatives through functional groups thereof. Such cargo molecules may be drugs with molecular weight ranging from 100 to 1500 g/mol, and may be polymer compounds such as peptides and nucleic acids.

In a preferred embodiment of the invention, the inositol derivative may be an inositol dimer coupled via a carbonate, carbamate, ester or amide link, having guanidinium side chains through varying chain lengths, as shown in formulae (II) to (IV).

The inositol derivative in accordance with the present invention can easily transport physiologically active molecules such as drugs, diagnostic reagents or fluorescent tags attached thereto across a biological membrane, e.g., plasma membrane, nuclear membrane and blood-brain barrier.

The inositol derivatives of formulae (II) to (IV) can be prepared by the following steps of:
(a) obtaining intermediates by protecting the hydroxyl groups of myo- or scyllo-inositol;
(b) obtaining inositol polymers by coupling two or more of the intermediates obtained in step (a);
(c) introducing one or more amino acid residues to the inositol polymer obtained in step (b) by acylation; and
(d) introducing guanidine groups to the amino acid N-terminal of the inositol polymer.

Specifically, in step (a), hydroxyl groups of myo- or scyllo-inositol are protected regioselectively according to any of the known methods, e.g., the method described in [Chung, Sung-Kee et al., Daewoo Science Book series, Natural Science 122, Minumsa (1998)]. Preferred intermediates obtained in step (a) are those of formulae (V) to (XI):

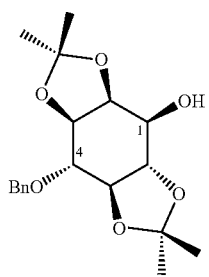

(V)

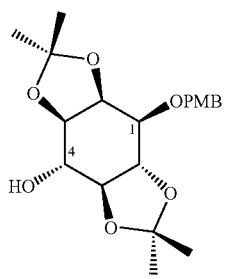

(VI)

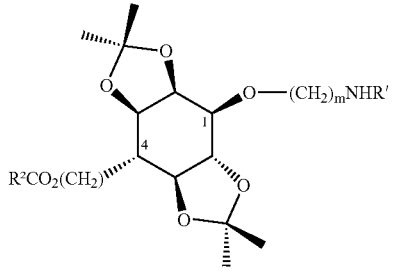

(VII)

-continued

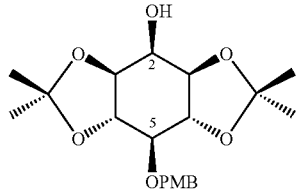

(VIII)

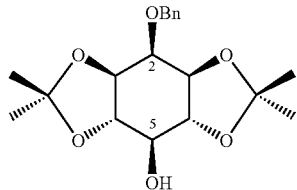

(IX)

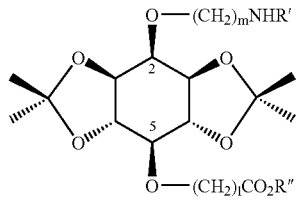

(X)

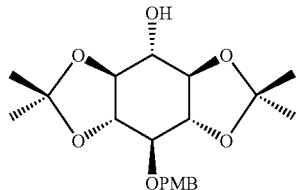

(XI)

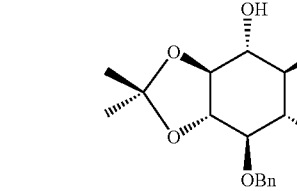

(XII)

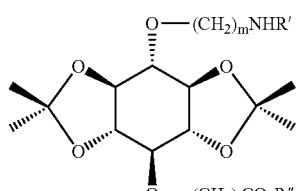

(XIII)

wherein R', R", l and m are the same as defined above, Bn is benzyl, and PMB is p-methoxybenzyl.

The compounds of formulae (V) to (VII) are intermediates for preparing the compound of formulae (II). The compounds of formulae (V) and (VI) may each be prepared by synthesizing 2,3:5,6-di-O-isopropylidene-myo-inositol from myo-inositol and protecting 1-OH or 4-OH thereof regioselectively with appropriate protecting groups, as shown in Scheme 1.

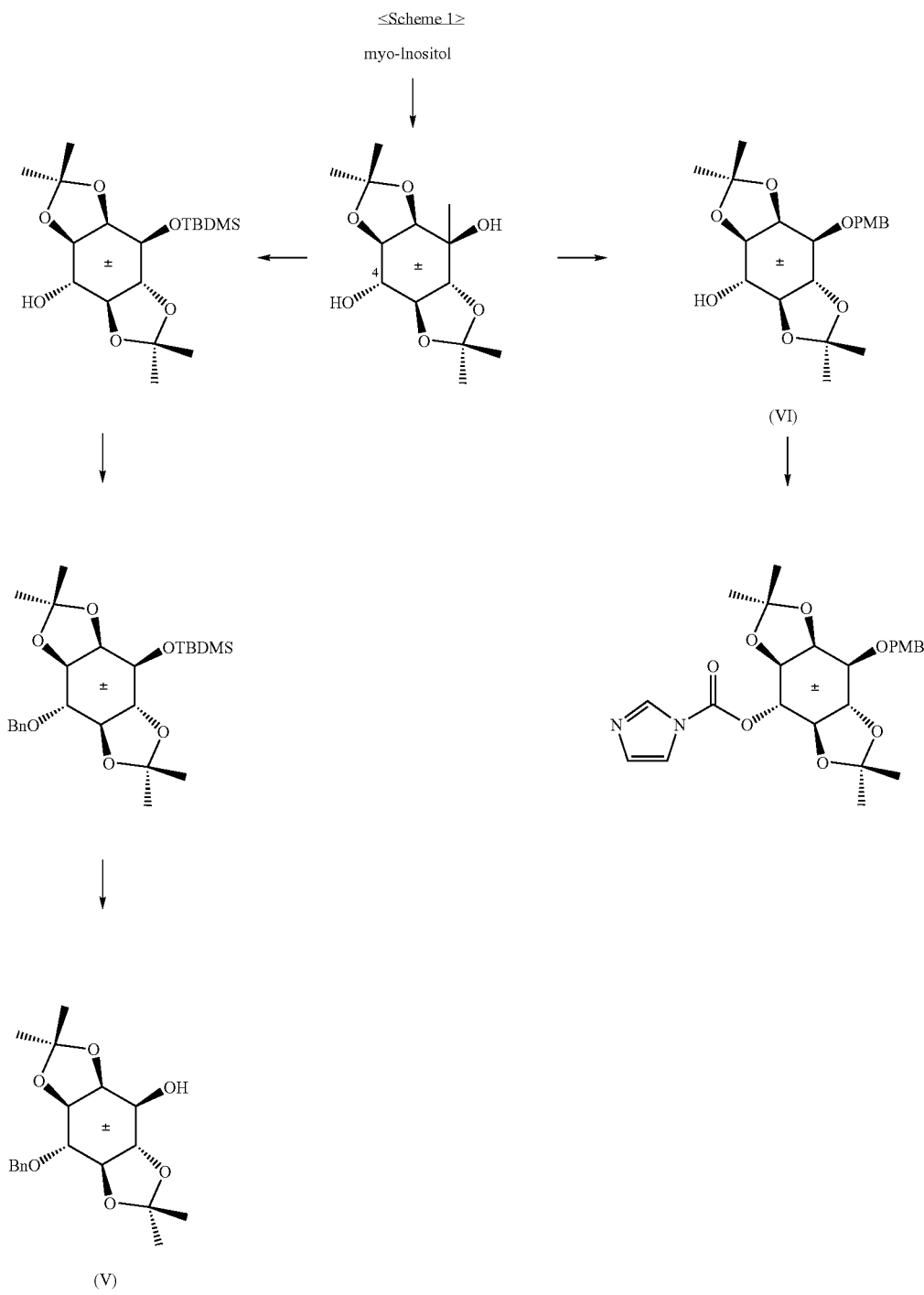

<Scheme 1> wherein TBDMS is tert-butyldimethylsilyl, PMB is p-methoxybenzyl and Bn is benzyl.

The use of myo-inositol, as a starting material for the preparation of compound of formula (II) is advantageous in terms of low price and simplicity of the preparation process. However, the compound of formula (II) prepared from myo-inositol is a diastereomeric mixture, as shown in Scheme 1. Accordingly, in order to avoid the complexity associated with the diastereomeric mixture, either of the compounds of formulae (III) and (IV) may be employed to prepare the compound of formula (I).

The compounds of formulae (VIII) to (X) are intermediates for preparing the compound of formulae (M). The compounds of formulae (VIII) and (IX) may be prepared by synthesizing 1,6:3,4-di-O-isopropylidene-myo-inositol from myo-inositol and protecting 2-OH or 5-OH thereof regioselectively with appropriate protecting groups, as shown in Scheme 2.

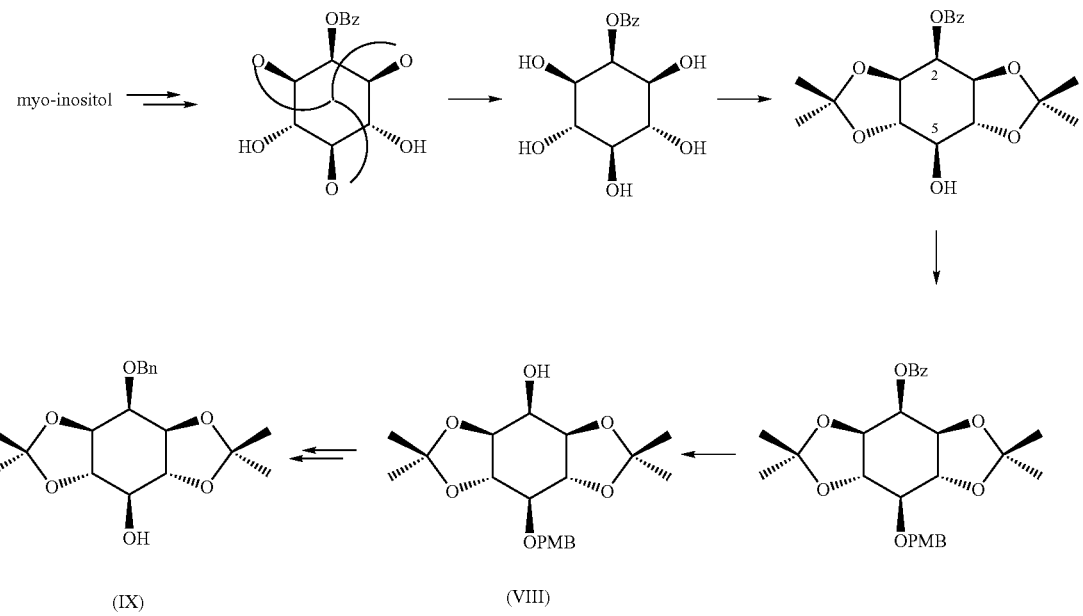

wherein Bz is benzoyl, and PMB and Bn are the same as defined in Scheme 1.

The compounds of formulae (XI) to (XIII) are intermediates for preparing the compound of formulae (IV). The compounds of formulae (I) and (XII) may each be prepared by synthesizing 1,6:3,4-di-O-isopropylidene-scyllo-inositol from myo-inositol by inversion of 2-OH via Mitsunobu reaction and protecting 2-OH or 5-OH thereof regioselectively with appropriate protecting groups, as shown in Scheme 3.

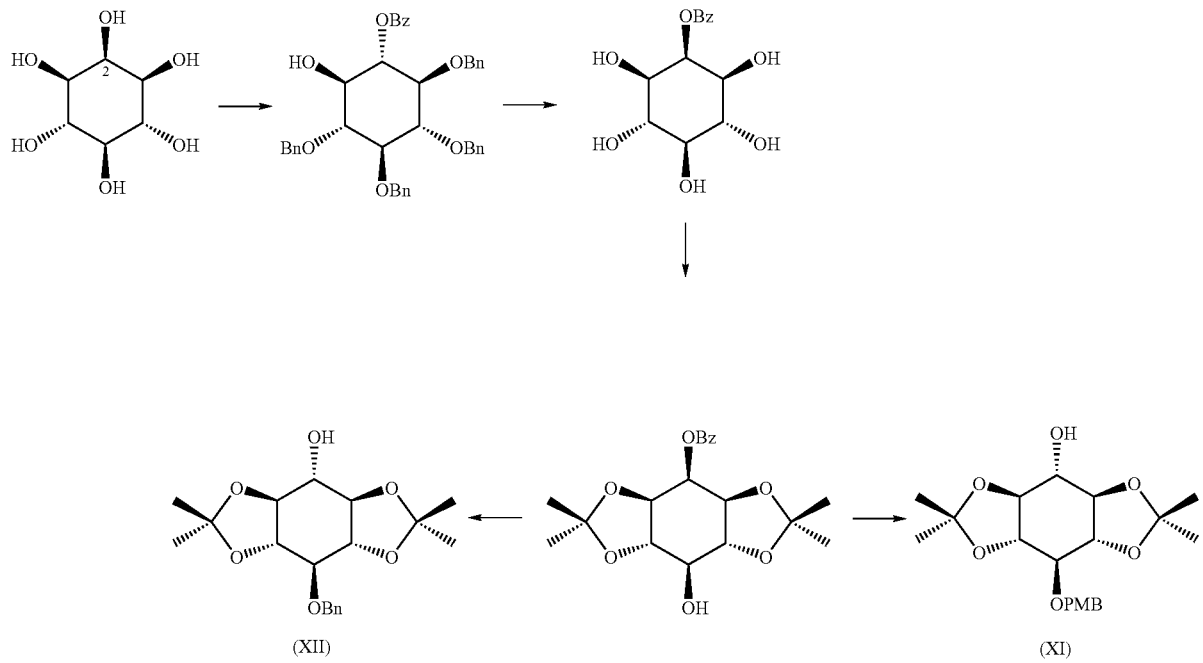

wherein Bz, Bn and PMB are the same as defined in Schemes 1 and 2.

In accordance with Schemes 2 or 3, a pure stereoisomer may be obtained.

Further, the compounds of formulae (VII), (X) and (XIII) containing carboxylate and amine groups may each be prepared by regioselectively alkylating the compound of formulae (V), (VI), (VIII), (IX), (XI) or (XII) having one (1) hydroxyl group. For example, the process for preparing the compound of formula (XIII) is shown in Scheme 4. The compounds of formulae (VII) and (X) may each be prepared in a similar manner.

available ω-amino acid, and preferred is an aminoalkanoic acid of formula (XIV) having the amino residue protected as described in [Protective Groups in Organic Synthesis 3$^{rd}$ Ed. T. W. Greene and P. G. M. Wuts, Wiley-Interscience, 1999]:

$$HO_2C-(CH_2)_n-NH\text{\textcircled{p}} \qquad (XIV)$$

wherein n is an integer in the range of 1 to 12, and \textcircled{p} is a protecting group.

The above acylation reaction may be performed having compound of formula (XIV) in an amount ranging from 10 to 20 equivalents based on 1 equivalent of the inositol polymer

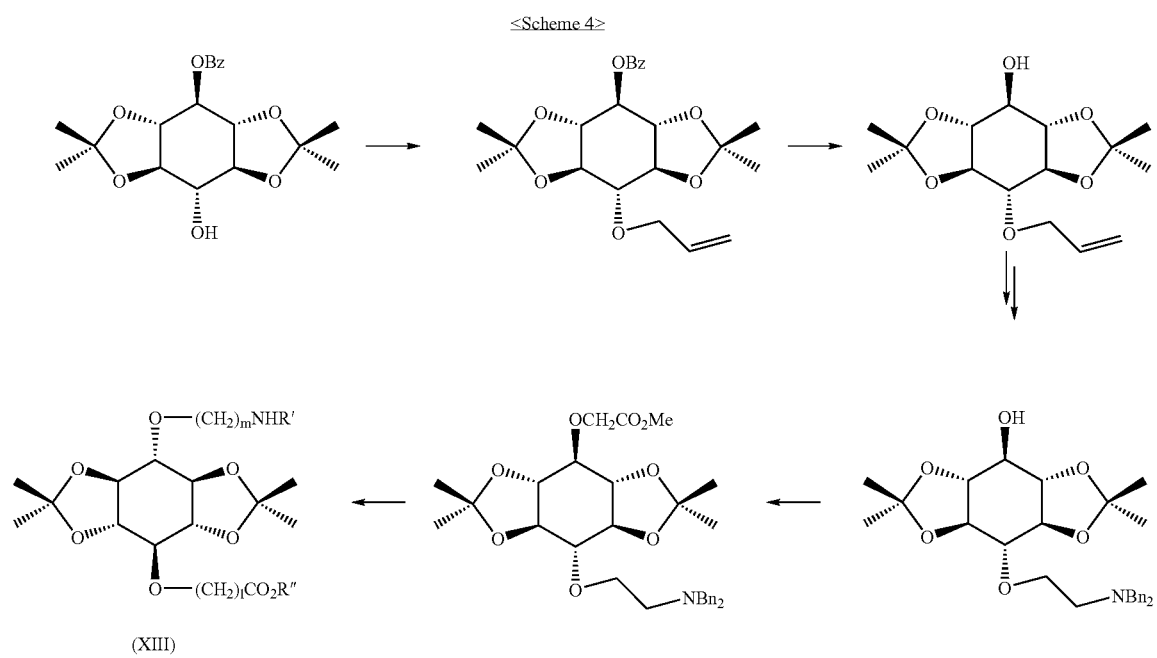

<Scheme 4> wherein R', R", l, m, Bn and Bz are the same as defined above.

In step (b), an inositol polymer may be prepared by coupling two or more intermediates obtained in step (a) according to the method described in [The Chemical Synthesis of Peptides, J. Jones, Clarendon Press, Oxford, 1991] using various functional groups (X and X') and then, removing the acetonide protecting groups. The functional groups (X and X') play the role of a linker in the coupling of inositol derivative units. Various linkers available in the relevant art may be used as X and X' in the present invention, especially —O—CO—O—, —O—CO—NH—$(CH_2)_m$—O—, —O—CO—$(CH_2)_l$—O— or —O—$(CH_2)_l$—CO—NH—$(CH_2)_m$—O— (wherein m is an integer in the range of 2 to 5, and l is an integer in the range of 1 to 5).

In step (c), one or more amino acids having various chain lengths may be introduced into the inositol polymer obtained in step (b) by way of using a condensing agent such as dicyclohexylcarbodiimide or 1-[3-(dimethylamino)propyl]]-ethylcarbodiimide hydrochloride.

The amino acid having a various side chain length used in the present invention may be obtained from commercially obtained in step (b) at a temperature ranging from 0 to 60° C., for a period ranging from 5 to 96 hours.

In step (d), a guanidinium group is introduced into the N-terminal of the amino acid residues of the inositol polymer after the amino acid protective group such as t-Boc (tert-butyloxycarbonyl group) is removed, by reacting the inositol polymer with N,N-di-Boc-N'-trifluoromethanesulfonylguanidine in the presence of a base in an organic solvent. N,N-di-Boc-N'-trifluoromethanesulfonylguanidine may be prepared according to the method described in [T. T. Baker et al., J. Org. Chem. 2000, 65, 9054], as shown in Preparation Examples 10 and 11.

Exemplary organic solvents that may be used in step (d) are dimethylformamide, chloroform and ethyl acetate, and the base may be triethylamine. The above reaction may be performed at a temperature ranging from 0 to 60° C. for a period ranging from 12 to 120 hours.

In steps (b) to (d), the intermediates of formulae (V) to (XIII) may be coupled in various combinations to give the compounds of formulae (II) to (IV). One embodiment of the method for preparing the inositol derivative in accordance with the present invention is shown in Scheme 5.

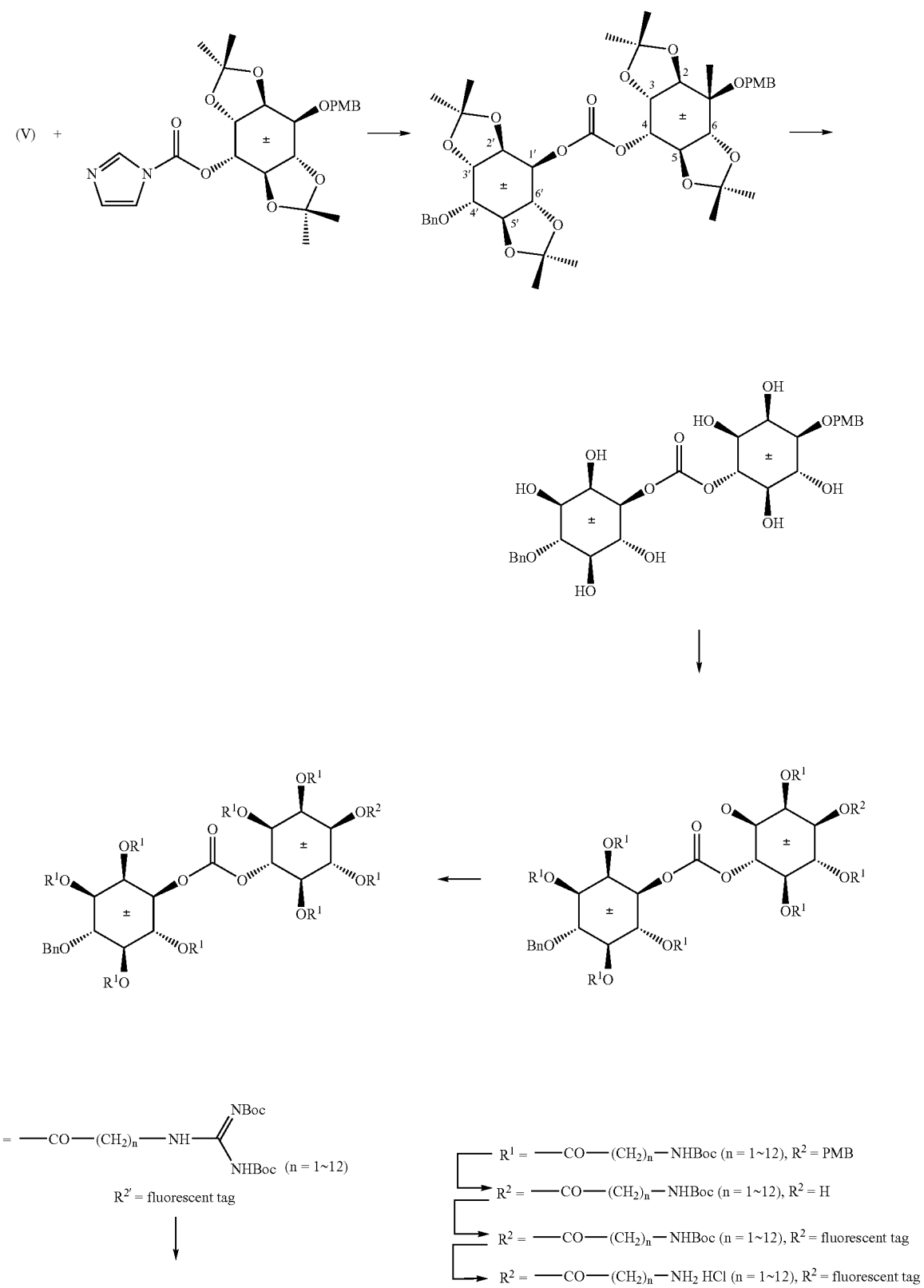

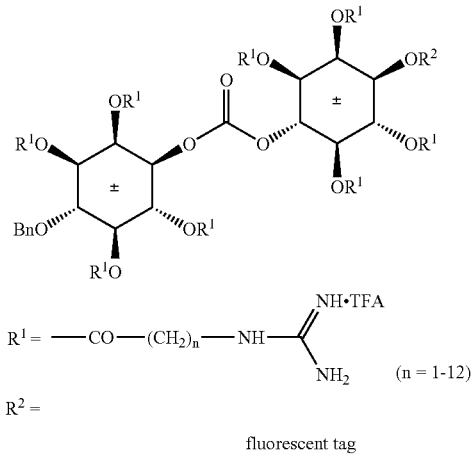

R¹ = —CO—(CH₂)ₙ—NH—C(=NH·TFA)NH₂  (n = 1-12)

R² = fluorescent tag wherein R¹, R² and n are the same as defined above.

As shown in Scheme 5, the inositol derivative having the form of inositol dimer coupled via a carbonate (X=—O—CO—O—) linker and carrying guanidine groups is prepared by coupling the compounds of formulae (V) and (VI) in the presence of a condensing agent. Specifically, the compound of formula (VI) is coupled to the compound of formula (V) and the acetonide protecting group is eliminated therefrom. Then, amino acids having various chain lengths (i.e., R¹) protected by t-Boc are introduced to the inositol dimer by way of acylation, the PMB protecting group is eliminated therefrom, and then, the inositol dimer is marked with a fluorescent tag such as dansyl (5-dimethylamino-1-naphthalenesulfonyl, i.e., R²) and FITC-I (fluorescein isothiocyanate). Thereafter, t-Boc protecting groups are eliminated and guanidinium groups are introduced to the deprotected amino acid N-terminals to obtain the inositol derivative of the present invention.

Further, a therapeutic molecule (a drug) or a diagnostic reagent (i.e., R³) can be conjugated to the inositol derivative after removing the benzyl protecting group, for example.

Inositol derivatives having inositol units linked to each other via ester (X=—O—CO—(CH₂)₁—O—), amide (X=—O—(CH₂)₁—CO—NH—(CH₂)ₘ—O—), and carbamate (X=—O—CO—NH—(CH₂)ₘ—O—) bridges can be prepared by the method described in [The Chemical Synthesis of Peptides, J. Jones, Clarendon Press, Oxford, 1991].

The inositol derivative of formula (I) of the present invention may be prepared from an intermediate other than the exemplified intermediates, the compounds of formulae (V) to (XIII), by a similar process comprising coupling and introducing amino acids having guanidinium groups.

The inositol derivative in accordance with the present invention may be a conjugate of a therapeutic molecule such as a drug and a diagnostic reagent. Therefore, the inositol derivative according to the present invention is effective in significantly enhancing the transportation of various therapeutic molecules across a biological membrane, which includes the plasma membrane, nuclear membrane or blood-brain barrier.

The following Examples are intended to further illustrate the present invention without limiting its scope.

PREPARATION EXAMPLE 1

(±)-1,4-Di-O-benzoyl-2,3:5,6-di-O-isopropylidene-myo-inositol

Myo-inositol (50 g, 278 mmol), 2,2-dimethoxypropane (150 ml, 1.2 mol) and p-toluenesulfonic acid (1 g, 5.2 mmol) were dissolved in dimethylformamide (200 ml) and refluxed at 100° C. for 21 hours. The mixture was cooled to room temperature, triethylamine (10 ml) was added thereto and filtered. Toluene (25 ml) was added to the filtrate and the solvent was removed under a reduced pressure. The resulting residue was dissolved in pyridine (150 ml), and then, benzoyl chloride (200 ml, 1.74 mol) was added dropwise thereto with a syringe at 0° C. over a period of 30 minutes. Thereafter, the mixture was stirred for 2 hours at room temperature, the precipitate formed was filtered, and washed successively with pyridine, water, acetone and diethyl ether, to obtain the title compound (35.55 g) as a white solid.

m.p.=322-325° C. ¹H-NMR (CDCl₃): 1.30, 1.43, 1.50, 1.63 (each s, 3H), 3.73 (dd, J=9.6 Hz, 11.1 Hz, 1H), 4.36 (dd, J=9.6 Hz, 10.6 Hz, 1H), 4.41 (dd, J=4.5 Hz, 9.6 Hz, 1H), 4.78 (dd, J=4.5 Hz, 4.5 Hz, 1H), 5.42 (dd, J=4.5 Hz, 10.6 Hz, 1H), 5.60 (dd, J=9.6 Hz, 11.1 Hz, 1H), 7.45 (m, 5H)

PREPARATION EXAMPLE 2

(±)-2,3:5,6-Di-O-isopropylidene-myo-inositol (±)-1,4-Di-O-benzoyl-2,3:5,6-di-O-isopropylidene-myo-inositol obtained in Preparation Example 1 (35.5 g, 75.8 mmol) and NaOCH₃ (2.41 g, 45.48 mmol) were dissolved in CH₃OH (500 ml) and refluxed for 16 hours. The mixture was cooled to room temperature, the solvent was evaporated off and then, CH₂Cl₂ (700 ml) was added thereto. The mixture was filtered through silica bed, and the filtrate was concentrated to obtain the title compound (18.21 g) as a white solid.

m.p.=169-171° C. ¹H-NMR (CDCl₃): 1.38, 1.46, 1.48, 1.54 (each s, 3H), 2.36 (d, J=8.8 Hz, 1H), 2.45 (d, J=2.9 Hz, 1H), 3.32 (dd, J=9.4 Hz, 10.5 Hz, 1H), 3.83 (dd, J=9.4 Hz, 9.4 Hz, 1H), 3.90 (ddd, J=2.9 Hz, 6.4 Hz, 10.5 Hz, 1H), 4.02 (ddd, J=4.8 Hz, 8.8 Hz, 9.4 Hz, 1H), 4.08 (dd, J=4.8 Hz, 6.4 Hz, 1H), 4.48 (dd, J=4.8 Hz, 4.8 Hz, 1H)

PREPARATION EXAMPLE 3

(±)-1-O-t-butyldimethylsilyl-2,3:5,6-di-O-isopropylidene-myo-inositol (±)-2,3:5,6-Di-O-isopropylidene-myo-inositol obtained in Preparation Example 2 (6 g, 23 mmol) and imidazole (5.2 g, 76 mmol) were dissolved in dimethylformamide (70 ml), and then, tert-butyldimethylsilyl chloride (3.8 g, 25 mmol) was added thereto at 0° C., followed by stirring the mixture at room temperature for 14 hours. The mixture was extracted with ethyl acetate and the extract was washed with saturated NaCl and NaHCO$_3$ solutions, dried over MgSO$_4$, and concentrated under a reduced pressure. The concentrate was purified using column chromatography (ethyl acetate:hexane=1:1 to 10) to obtain the title compound (5.84 g) as a white solid.

m.p.=148-150° C. $^1$H-NMR (CDCl$_3$): 0.14 (s, 6H), 0.93 (s, 9H), 1.35, 1.42, 1.44, 1.53 (each s, 3H), 2.87 (brs, 1H), 3.26 (dd, J=9.4 Hz, 10.4 Hz, 1H), 3.87 (dd, J=6.4 Hz, 10.4 Hz, 1H), 3.90 (dd, J=9.4 Hz, 10.4 Hz, 1H), 3.97 (dd, J=4.4 Hz, 4.6 Hz, 1H), 4.03 (dd, J=4.4 Hz, 10.4 Hz, 1H), 4.29 (dd, J=4.4 Hz, 4.4 Hz, 1H)

PREPARATION EXAMPLE 4

(±)-4-O-benzyl-2,3:5,6-di-O-isopropylidene-1-O-t-butyldimethylsilyl-myo-inositol (±)-1-O-t-butyldimethylsilyl-2,3:5,6-di-O-isopropylidene-myo-inositol obtained in Preparation Example 3 (5.76 g, 15 mmol) was dissolved in CH$_2$Cl$_2$ (100 ml), and then, silver oxide (I) (10.7 g, 46 mmol), benzyl bromide (5.47 ml, 46 mmol) and tetrabutylammonium iodide (0.55 g, 1.5 mmol) were added thereto, followed by stirring the mixture at room temperature for 2 hours. The resulting solution was filtered through celite, washed with CH$_2$Cl$_2$, and then, concentrated under a reduced pressure. The concentrate was purified using column chromatography (ethyl acetate:hexane=1:40) to obtain the title compound (4.91 g) as a white solid.

m.p.=89° C. $^1$H-NMR (CDCl$_3$): 0.12 (s, 6H), 0.90 (s, 9H), 1.31, 1.35, 1.40, 1.41 (each s, 3H), 3.31 (t, J=9.7 Hz, 1H), 3.65 (dd, J=6.6 Hz, 10.4 Hz, 1H), 3.85 (t, J=9.3 Hz, 1H), 3.98 (dd, J=4.3 Hz, 10.1 Hz, 1H), 4.07 (t, J=5.6 Hz, 1H), 4.27 (t, J=5.6 Hz, 1H), 4.80 (s, 2H), 7.21-7.40 (m, 5H) MS (FAB) m/z 465.21 (M$^+$+H)

PREPARATION EXAMPLE 5

(±)-4-O-benzyl-2,3:5,6-di-O-isopropylidene-myo-inositol [Compound of Formula (V)]

(±)-4-O-benzyl-2,3:5,6-di-O-isopropylidene-1-O-t-butyldimethylsilyl-inyo-inositol obtained in Preparation Example 4 (4.6 g, 9.9 mmol) was dissolved in tetrahydrofuran, and then, tetrabutylammonium fluoride (1.0 M solution in THF, 29.7 ml, 29.7 mmol) was added thereto, followed by stirring the mixture at room temperature for 7 hours. The resultant was extracted with ethyl acetate and the extract was washed with saturated NaCl. The organic layer was dried over MgSO$_4$ and concentrated. The concentrate was crystallized from hexane to obtain the title compound (3.7 g) as a white solid.

m.p.=131° C. $^1$H-NMR (CDCl$_3$): 1.33, 1.36, 1.43, 1.46 (each s, 3H), 2.40 (d, J=8.4 Hz, 1H), 3.39 (t, J=9.6 Hz, 1H), 3.65 (dd, J=6.4 Hz, 10.4 Hz, 1H), 3.78 (t, J=9.8 Hz, 1H), 3.94-4.02 (m, 1H), 4.18 (t, J=5.6 Hz, 1H), 4.24 (t, J=4.9 Hz, 1H), 4.80 (s, 2H), 7.22-7.40 (m, 5H)

PREPARATION EXAMPLE 6

(±)-1-O-p-methoxybenzyl-2,3:5,6-di-O-isopropylidene-myo-inositol [Compound of Formula (VI)]

(±)-2,3:5,6-Di-O-isopropylidene-myo-inositol obtained in Preparation Example 2 (5.59 g, 20 mmol) was dissolved in dimethylformamide (90 ml), and then NaH (0.96 g, 40 mmol) and p-methoxybenyl chloride (3.2 ml, 24 mmol) were added thereto, followed by stirring the mixture at room temperature. At the completion of the reaction after 10 hours, reaction mixture was quenched with water at 0° C. The resultant was extracted with CH$_2$Cl$_2$ and the extract was washed with saturated NaHCO$_3$. The organic layer was dried over MgSO$_4$ and concentrated. The concentrate was purified using column chromatography (ethyl acetate:hexane=1:1 to 2) to obtain the title compound (2.2 g) as a white solid.

m.p.=153-154° C. $^1$H-NMR (CDCl$_3$): 1.32, 1.44, 1.46, 1.52 (each s, 3H), 2.27 (d, J=2.5 Hz), 3.24 (dd, J=10.1 Hz, 10.1 Hz, 1H), 3.75 (dd, J=4.3 Hz, 10.1 Hz, 1H), 3.79 (s, 3H), 3.83-3.92 (m, 2H), 4.01 (dd, J=10.1 Hz, 10.1 Hz, 1H), 4.27 (dd, J=4.3 Hz, 4.3 Hz, 1H), 4.71 (dd, J=12.1 Hz, 1H), 4.82 (d, J=12.1 Hz, 1H), 6.86 (d, J=8.6 Hz, 2H), 7.32 (d, J=8.6 Hz, 2H)

PREPARATION EXAMPLE 7

4-Boc-aminobutanoic acid

4-Aminobutanoic acid (1 g, 9.7 mmol) was dissolved in tert-butyl alcohol (15 ml), 5N NaOH (1.93 ml, 9.7 mmol) was added thereto, and the mixture was stirred at room temperature for 10 minutes. Di-tert-butyl-dicarbonate (2.33 g, 10.7 mmol) dissolved in tert-butylalcohol (17 ml) was added thereto and stirred for 24 hours at room temperature. Water (12 ml) was added thereto and the resultant was concentrated under a reduced pressure and cooled to 0° C. Then, 2N H$_2$SO$_4$ was added thereto dropwise until pH of the mixture became 2. The resultant was extracted with ethyl acetate and the extract was washed with water. The organic layer was dried over MgSO$_4$ and concentrated to obtain the title compound (2.1 g) as a white solid.

m.p.=57-58° C. $^1$H-NMR (CDCl$_3$): 1.45 (s, 9H), 3.19 (m, 2H), 4.70 (brs, 1H) MS (FAB) m/z 226.07 (M$^+$+Na)

PREPARATION EXAMPLE 8

6-Boc-aminohexanoic acid

6-Aminocaproic acid (10 g, 76 mmo) was dissolved in tert-butylalcohol (100 ml), 5N NaOH (15 ml, 76 mmol) was added thereto, and the mixture was stirred at room temperature for 10 minutes. Di-tert-butyl-dicarbonate (18.3 g, 83 mmol) dissolved in tert-butylalcohol (100 ml) was added thereto and stirred at room temperature for 24 hours. Then, water (100 ml) was added thereto and the mixture was concentrated under a reduced pressure, cooled to 0° C., and then, 2N H$_2$SO$_4$ was added thereto dropwise until pH of the mixture became 2. Thereafter, the resultant was extracted with ethyl acetate, the extract was washed with water, dried over MgSO$_4$ and concentrated. The concentrate was purified using column chromatography (ethyl acetate:toluene:acetic acid=20:10:0.3) to obtain the title compound (17.9 g) as a white solid.

m.p.=38-39° C. $^1$H-NMR (CDCl$_3$): 1.30 (m, 2H), 1.40 (s, 9H), 1.50 (m, 2H), 2.28 (t, J=7.4 Hz, 2H), 3.01 (m, 2H) MS (FAB) m/z 254.09 (M$^+$+Na)

PREPARATION EXAMPLE 9

8-Boc-aminooctanoic acid

8-Aminocaprylic acid (970.3 mg, 6.1 mmol) was dissolved in tert-butylalcohol (14.7 ml), 5N NaOH (1.44 ml, 6.1 mmol) was added thereto, and the mixture was stirred at room temperature for 10 minutes. Di-tert-butyl-dicarbonate (1.46 g, 6.7 mmol) dissolved in tert-butylalcohol (10 ml) was added thereto and stirred at room temperature for 24 hours. Then, water (10 ml) was added thereto and the mixture was concentrated under a reduced pressure, cooled to 0° C., and then, 2N H$_2$SO$_4$ was added thereto dropwise until pH of the mixture became 2. The resultant was extracted with ethyl acetate, the extract was washed with H$_2$O, dried over MgSO$_4$ and concentrated. The concentrate was purified using column chromatography (ethyl acetate:toluene:acetic acid=20:10:0.3) to obtain the title compound (1.78 g) as a white solid.

m.p.=57-58° C. $^1$H-NMR (CDCl$_3$): 1.30 (m, 6H), 1.45 (s, 9H), 1.46 (m, 2H), 1.63 (m, 2H), 2.34 (t, J=7.4 Hz, 2H), 3.10 (m, 2H) MS (FAB) m/z 282.18 (M$^+$+Na)

PREPARATION EXAMPLE 10

N,N-Bis-Boc-guanidine

Guanidine hydrochloride (4 g, 42 mmol) and 4N NaOH (42 ml, 0.1 mol) were dissolved in 1,4-dioxane (80 ml) and cooled to 0° C. Di-tert-butyl-dicarbonate (20 g, 92.1 mol) was added thereto and warmed to room temperature, followed by stirring the mixture for 18 hours. The solvent was evaporated off until the volume thereof became ⅓, and then, water added thereto. The resultant was extracted with ethyl acetate, and the extract was washed successively with 10% citric acid, H$_2$O and saturated NaCl, dried over MgSO$_4$, and concentrated. The concentrate was purified using column chromatography (CH$_2$Cl$_2$:MeOH=20:1) to obtain the title compound (6.47 g).

m.p.=144-145° C. $^1$H-NMR (DMSO-d$_6$): 1.39 (s, 18H), 8.47 (brs, 2H), 10.42 (brs, 1H)

PREPARATION EXAMPLE 11

N,N-Di-Boc-N'-trifluoromethanesulfonylguanidine

N,N-Bis-Boc-guanidine obtained in Preparation Example 10 (6.05 g, 23 mmol) was dissolved in CH$_2$Cl$_2$ (40 ml), triethylamine (4.8 ml, 34.5 mmol) was added thereto. Triflic anhydride (3.9 ml, 25.3 mmol) was added dropwise to the mixture with a syringe at −78° C. and warmed to room temperature over 4 hours followed by stirring at room temperature for 3 hours. The resulting solution was washed with 2N H$_2$SO$_4$ and water, dried over Na$_2$SO$_4$ and concentrated. The concentrate was purified using column chromatography (CH$_2$Cl$_2$), crystallized from hexane to obtain the title compound (7.09 g) as a white solid.

m.p.=114-115° C. $^1$H-NMR (DMSO-d$_6$): 1.45 (s, 18H), 11.45 (brs, 2H) MS (FAB) m/z 392.03 (M$^+$+H), 414.16 (M$^+$+Na)

PREPARATION EXAMPLE 12

2-O-benzoyl-myo-inositol orthoformate

Myo-inositol (50 g, 278 mmol), trimethyl orthoformate (63 ml, 570 mmol) and p-toluenesulfonic acid (2.0 g) were dissolved in dimethylformamide (200 ml), stirred at 120° C. for 7 hours and the resulting solution was evaporated off at 50° C. over 2 hours. Pyridine (100 ml) and then benzoyl chloride (35 ml, 299 mmol) were added thereto dropwise at 0° C., followed by stirring the mixture at room temperature for a day. Distilled water (10 ml) was added to the mixture, stirred for 30 minutes, diluted with ethyl acetate and washed successively with saturated NaHSO$_4$, NaHCO$_3$ and NaCl. The organic layer was dried over MgSO$_4$, filtered, concentrated and the concentrate was crystallized from ethyl acetate to obtain the title compound (35.5 g) as a white solid.

m.p.=206-207° C. $^1$H-NMR(acetone-d$_6$, with drops of D$_2$O): δ4.26 (m, 1H), 4.37 (m, 2H), 4.50 (t, J=3.8 Hz, 2H), 5.52 (d, J=1.3 Hz, 1H), 5.57 (app q, J=1.9 Hz, 1H), 7.50-8.11 (m, 5H)

PREPARATION EXAMPLE 13

2-O-benzoyl-myo-inositol

2-O-benzoyl-myo-inositol orthoformate obtained in Preparation Example 12 (10 g, 34 mmol) was dissolved in CH$_3$OH (200 ml), p-toluenesulfonic acid (646 mg, 3.4 mmol) was added thereto, followed by stirring the mixture at 60° C. for 3 hours. The mixture was cooled to room temperature, left for a day and crystallized. The precipitation formed was filtered, washed with CH$_3$OH and ethyl acetate to obtain the title compound (8 g) as a white solid.

m.p.=240-242° C. $^1$H-NMR(CD$_3$OD-DMSO-d$_6$): δ 3.30 (t, J=8.9 Hz, 1H), 3.66 (dd, J=2.6, 9.7 Hz, 2H), 3.73 (dd, J=8.9 Hz, 9.7 Hz, 2H), 5.69 (t, J=2.6 Hz, 1H), 7.51-8.09 (m, 5H)

PREPARATION EXAMPLE 14

2-O-benzoyl-1,6:3,4-di-O-isopropylidene-myo-inositol

2-O-benzoyl-myo-inositol obtained in Preparation Example 13 (5.0 g, 17.6 mmol) and 2-methoxypropene (10.1 ml, 105.5 mmol) were dissolved in dimethylformamide (100 ml), p-toluenesulfonic acid (335 mg, 1.76 mmol) was added in portions thereto at 0° C., followed by stirring the mixture at room temperature for 20 hours. The mixture was poured to saturated NaHCO$_3$ solution (200 ml), extracted with ethyl acetate (400 ml), and the extract was washed with saturated aq. NaCl (400 ml). The organic layer was dried over MgSO$_4$, concentrated, and purified using column chromatography (ethyl acetate:hexane=1:3 to 1:1) and fractional crystallization (ethyl acetate and n-hexane) to obtain the title compound (2 g) as a white solid.

m.p.=181-183° C. $^1$H-NMR(CDCl$_3$): δ 1.40, 1.48 (each s, 6H), 2.97 (d, J=1.5 Hz, 1H), 3.83 (dd, J=2.1 Hz, 8.4 Hz, 2H), 4.09-4.15 (m, 3H), 6.06 (t, J=2.1 Hz, 1H), 7.47-8.09 (m, 5H) MS (FAB) m/z 387 (M$^+$+Na), 365 (M$^+$+H)

PREPARATION EXAMPLE 15

(±)-2,3-O-isopropylidene-myo-inositol

Myo-inositol (50 g, 277 mmol), 2,2-dimethoxypropane (85 ml, 691 mmol) and p-toluenesulfonic acid (500 mg, 2.6 mmol) were dissolved in dimethylsulfoxide (160 ml), followed by stirring the mixture at 90 to 100° C. for an hour. The mixture was cooled to 20° C., and ethyl alcohol (200 ml) and ether (1 L) were added thereto, followed by stirring the mixture for 2 hours. Triethylamine (10 ml) was added thereto, and the mixture was stirred for 4 hour. After completion of the reaction, the mixture was filtered, washed with CH$_3$OH/ether (1:5, 240 ml) and crystallized using ethanol to obtain the title compound (51 g) as a white solid.

m.p.=165-166° C. $^1$H-NMR (CDCl$_3$): δ 1.32, 1.47 (each s, 3H), 3.09 (app. t, J=9.1 Hz, 1H), 3.53 (dd, J=9 Hz, 9.3 Hz, 2H), 3.90 (app.t, J=8.7 Hz, 1H), 4.34 (app. t, J=9.3 Hz, 1H)

PREPARATION EXAMPLE 16

(±)-1,4,5,6-Tetra-O-benzyl-2,3-O-isopropylidene-myo-inositol (±)-2,3-O-isopropylidene-myo-inositol obtained in Preparation Example 15 (20 g, 90.8 mmol) and NaH (47.5 g, 1090 mmol) were dissolved in dimethylformamide (600 ml), benzyl bromide (108.02 ml, 908 mmol) was added thereto at 0° C., followed by stirring the mixture for 2 hours. The resulting solution was warmed to room temperature, stirred for 20 hours. After completion of the reaction, the mixture was extracted with ethyl acetate, the extract was washed with saturated NaHCO$_3$ and NaCl, and dried over MgSO$_4$. The resultant was evaporated off and purified using column chromatography (ethyl acetate:hexane=1:9) to obtain the title compound (45 g) as a syrup.

$^1$H-NMR (CDCl$_3$): δ 1.37, 1.55 (each s, 3H), 3.42 (t, J=8.7 Hz, 1H), 3.88 (dd, J=3.7 Hz, 8.8 Hz, 1H), 3.79 (dd, J=7.0 Hz, 9.5 Hz, 1H), 3.99 (app. t, J=8.5 Hz, 1H), 4.10 (app. t, J=6.2 Hz, 1H), 4.27 (dd, J=3.8 Hz, 5.5 Hz, 1H), 4.72-4.90 (m, 8H), 7.22-7.40 (m, 20H) MS (FAB) m/z 603 (M$^+$+Na)

PREPARATION EXAMPLE 17

(±)-1,4,5,6-Tetra-O-benzyl-myo-inositol (±)-1,4,5,6-Tetra-O-benzyl-2,3-O-isopropylidene-myo-inosistol obtained in Preparation Example 16 (42 g, 72.38 mmol) was dissolved in 80% acetic acid solution (290 ml), stirred at 100° C. for 3 hours, and the solvent was evaporated off and concentrated. The concentrate was crystallized from ethyl acetate-hexane (1:2) solution to obtain the title compound (36.5 g) as a white solid.

m.p.=126.5-127° C. $^1$H-NMR (CDCl$_3$): δ 2.40 (d, 4.5 Hz, 1H), 2.45 (s, 1H), 3.44-3.51 (m, 3H), 3.85 (app. t, J=9.5 Hz, 1H), 4.0 (app. t, J=9.5 Hz, 1H), 4.21 (br s, 1H), 4.7-4.97 (m, 8H), 7.25-7.40 (m, 20H) MS (FAB) m/z 563 (M$^+$+Na)

PREPARATION EXAMPLE 18

(±)-1-O-benzoyl-2,3,4,5-tetra-O-benzyl-scyllo-inositol (±)-1,4,5,6-Tetra-O-benzyl-2,3-O-isopropylidene-myo-inositol obtained in Preparation Example 17 (30 g, 55.53 mmol), triphenylphosphine (17.5 g, 66.63 mmol), benzoic acid (8.1 g, 66.63 mmol) and diethyl azodicarboxylate (10.5 ml, 66.63 mmol) were dissolved in toluene (300 ml) and stirred at 80 to 85° C. for 4 hours. After completion of the reaction, the solvent was evaporated off and the product was purified using column chromatography (ethyl acetate:hexane=1:2) to obtain the title compound (30.8 g) as a solid.

m.p.=135-136° C. $^1$H-NMR (CDCl$_3$): δ 2.45 (s, 1H), 3.55-3.77 (m, 5H), 4.7-5.0 (m, 8H), 5.39 (app. t, J=9.8 Hz, 1H), 7.10-8.05 (m, 25H) MS (FAB) m/z 667 (M$^+$+Na)

PREPARATION EXAMPLE 19

1-O-benzoyl-scyllo-inositol (±)-1-O-benzoyl-2,3,4,5-tetra-O-benzyl-scyllo-inositol obtained in Preparation Example 18 (8 g, 12.4 mmol) and 20% Pd(OH)$_2$/C (4.3 g) in CH$_2$Cl$_2$/CH$_3$OH (1:2, 210 ml) solution were shaken under H$_2$ (50 psi) for 24 hours. The mixture was filtered, and the filtrate was evaporated off and the product was crystallized from CH$_3$OH to obtain the title compound (3.6 g) as white solid.

m.p.=245-247° C. $^1$H-NMR (CD$_3$OD): δ 3.30-3.40 (m, 3H), 3.55 (app. t, J=9.2 Hz, 2H), 5.1 (t, J=9.7 Hz, 1H), 7.45-8.1 (m, 5H) MS (EI) m/z 284 (M$^+$)

PREPARATION EXAMPLE 20

1-O-benzoyl-2,3:5,6-di-O-isopropylidene-scyllo-inositol

1-O-benzoyl-scyllo-inositol obtained in Preparation Example 19 (6 g, 21.11 mmol) and p-toluenesulfonic acid (400 mg, 2.1 mmol) were dissolved in dimethylformamide (100 ml), 2-methoxypropene (20.2 ml, 211.14 mmol) was added dropwise thereto at room temperature over a period of 30 minutes. The mixture was stirred for 22 hours at room temperature and then poured into saturated NaHCO$_3$ solution, followed by vigorous stirring the mixture. The resulting solution was extracted with ethyl acetate, the extract was dried over MgSO$_4$ and evaporated off. The crude residue was crystallized from ethyl acetate-hexane (2:1) and purified by column chromatography (ethyl acetate:hexane=1:1) to obtain the title compound (2.1 g).

m.p.=284-286° C. $^1$H-NMR (CDCl$_3$): δ 1.44, 1.48 (each s, 3H), 2.46 (d, J=2.8 Hz, 1H), 3.76 (app. t, J=9.4 Hz, 2H), 3.88 (app.t, J=9.4 Hz, 2H), 4.13 (dt, J=2.8 Hz, 8.8 Hz), 5.7 (t, J=9.3 Hz, 1H), 7.27-8.1 (m, 5H) MS (FAB) m/z 365 (M$^+$+Na)

PREPARATION EXAMPLE 21

4-O-(1'-imidazolylcarbonyl)-2,3:5,6-di-O-isopropylidene-1-O-p-methoxybenzyl-myo-inositol 1-O-p-methoxybenzyl-2,3:5,6-di-O-isopropylidene-myo-inositol obtained in Preparation Example 20 (2.2 g, 5.8 mmol) was dissolved in toluene (40 ml), CaH$_2$ (0.59 g, 13.3 mmol) and carbonyldiimidazole (2.35 g, 15.4 mmol) were added thereto, followed by stirring the mixture for 11 hours at room temperature. The mixture was filtered and filtrate was evaporated off, and the product was purified using column chromatography (ethyl acetate:hexane=1:1) to obtain the title compound as a white solid (2.6 g).

m.p.=144-145° C. $^1$H-NMR (CDCl$_3$): 1.35, 1.46, 1.45, 1.63 (each s, 3H), 3.49 (dd, J=9.3 Hz, 11.4 Hz, 1H), 3.80 (s, 3H), 3.84 (d, J=4.2 Hz, 1H), 4.17 (dd, J=2.4 Hz, 5.4 Hz, 1H), 4.21 (d, J=9.6 Hz, 1H), 4.32 (dd, J=4.5 Hz, 1H), 4.74 (d, J=12.0 Hz, 1H), 4.86 (d, J=12.0 Hz, 1H), 5.35 (dd, J=6.9 Hz, 11.1 Hz, 1H), 6.89 (d, J=8.7 Hz, 2H), 7.05 (dd, J=0.6 Hz, 1.5 Hz, 1H), 7.35 (d, J=8.7 Hz, 2H), 7.42 (dd, J=1.5 Hz, 1H), 8.12 (s, 1H) MS (FAB) m/z 497 (M$^+$+Na)

PREPARATION EXAMPLE 22

2-O-benzoyl-1,6:3,4-di-O-isopropylidene-5-O-p-methoxybenzyl-myo-inositol

2-O-benzoyl-1,6:3,4-di-O-isopropylidene-myo-inositol obtained in Preparation Example 14 (1 g, 2.74 mmol), Ag$_2$O (1.27 g, 5.49 mmol), p-methoxybenzyl chloride (744 μl, 5.49 mmol), molecular sieve 4 Å (powder, 1 g) and tetrabutylammonium iodide (101 mg, 274 μmol) were dissolved in CH$_2$Cl$_2$ (10 ml) and stirred at room temperature for 30 hours. Then, the product was purified using column chromatography (ethyl acetate:hexane=1:2), and recrystallized using ethyl acetate and hexane to obtain the title compound (837 mg) as a white solid.

m.p.=150-152° C. $^1$H-NMR(CDCl$_3$): δ 1.35, 1.44 (each s, 6H), 3.77 (dd, J=9.5 Hz, 2.0 Hz, 2H), 3.80 (s, 3H), 3.87 (t, J=9.1 Hz, 1H), 4.15 (t, J=9.3 Hz, 1H), 4.80 (s, 2H), 6.0 (t, J=1.9 Hz, 1H), 6.87 (d, J=8.8 Hz, 2H), 7.35-7.57 (m, 5H), 8.0 (d, J=8.3 Hz, 2H) MS (FAB) m/z 507 (M$^+$+Na), 485 (M$^+$+H)

PREPARATION EXAMPLE 23

1,6:3,4-Di-O-isopropylidene-5-O-p-methoxybenzyl-myo-inositol [Compound of Formula (VII)]

2-O-benzoyl-1,6:3,4-di-O-isopropylidene-5-O-p-methoxybenzyl-myo-inositol obtained in Preparation Example 22 (700 mg, 1.45 mmol) was dissolved in CH$_3$OH (15 ml), NaOCH$_3$ (66 μl, 25% in CH$_3$OH, 0.29 mmol) was added thereto and refluxed for 2 hours. The resulting solution was cooled to room temperature and left for a day. The precipitate formed was filtered and the filtrate was washed with CH$_3$OH and ethyl acetate to obtain the title compound (484 mg) as a white solid.

m.p.=191-192° C. $^1$H-NMR(CDCl$_3$): δ 1.48, 1.50 (each s, 6H), 2.22 (brs, 1H), 3.59 (dd, J=9.4 Hz, 2.1 Hz, 2H), 3.82 (s, 3H), 3.82 (t, J=9.4 Hz, 1H), 4.12 (t, J=9.3 Hz, 2H), 4.58 (broad d, J=1.9 Hz, 1H), 4.80 (s, 2H), 6.89 (d, J=8.6 Hz, 2H), 7.37 (d, J=8.6 Hz, 2H) MS (FAB) m/z 403 (M$^+$+Na)

PREPARATION EXAMPLE 24

2-O-benzyl-1,6:3,4-di-O-isopropylidene-5-O-p-methoxybenzyl-myo-inositol 1,6:3,4-Di-O-isopropylidene-5-O-p-methoxybenzyl-myo-inositol obtained in Preparation Example 23 (280 mg, 0.736 mmol) was dissolved in dimethylformamide (5 ml), NaH (70 mg, 55%, 1.47 mmol in mineral oil) was added thereto at 0° C. and warmed to room temperature, followed by stirring the mixture for 30 minutes. Benzyl bromide (256 mg, 1.47 mmol) was added thereto, stirred at room temperature for 1 hour and saturated NaHCO$_3$ (50 ml) was added thereto to terminate the reaction. The resultant was diluted using ethyl acetate (300 ml), washed with saturated NaHCO$_3$ (50 ml) and NaCl (50 ml), and the organic layer was dried over Na$_2$SO$_4$ and purified using column chromatography (ethyl acetate:hexane=1:2) to obtain the title compound (320 mg) as a white solid.

m.p.=180-181° C. $^1$H-NMR(CDCl$_3$): δ 1.47, 1.48 (each s, 6H), 3.62 (dd, J=9.5 Hz, 2.0 Hz, 2H), 3.80 (t, J=9.2 Hz, 1H), 3.82 (s, 3H), 4.20 (t, J=9.3 Hz, 2H), 4.37 (t, J=2.0 Hz, 1H), 4.80, 4.85 (2s, 4H), 6.90 (dm, J=6.7 Hz, 2H), 7.27-7.39 (m, 8H) MS (FAB) m/z=493 (M$^+$+Na)

PREPARATION EXAMPLE 25

2-O-benzyl-1,6:3,4-di-O-isopropylidene-myo-inositol [Compound of Formula (IX)]

2-O-benzyl-1,6:3,4-di-O-isopropylidene-5-O-p-methoxybenzyl-myo-inositol obtained in Preparation Example 24 (283 mg, 0.60 mmol) was dissolved in CH$_2$Cl$_2$, Mn(OAc)$_3$ (449 mg, 1.8 mmol), 2,3-dichloro-5,6-dicyano-1,4-benzoquinone (147 mg, 0.65 mmol) were added thereto at room temperature and stirred for 12 hours. Saturated NaHCO$_3$ (30 ml) was slowly added thereto, and diluted with ethyl acetate (50 ml). The organic layer was washed with distilled water (30 ml×2 times) and brine, dried over Na$_2$SO$_4$, evaporated and purified using column chromatography (ethyl acetate: hexane=1:2 to 1:1) to obtain the title compound (176 mg) as a white solid.

m.p.=190-191° C. $^1$H-NMR(CDCl$_3$): δ 1.48, 1.49(2s, 12H), 2.44 (brs, 1H), 3.64 (dd, J=9.1 Hz, 1.9 Hz, 2H), 4.02 (m, 1H), 4.13(t, J=9.4 Hz, 2H), 4.40 (t, J=2.0 Hz, 1H), 4.85 (s, 2H), 6.90 (dm, J=6.7 Hz, 2H), 7.27-7.40 (m, 5H) MS (FAB) m/z 373 (M$^+$+Na)

PREPARATION EXAMPLE 26

2-O-(1'-imidazolylcarbonyl)-5-O-p-methoxybenzyl-1,6:3,4-di-O-isopropylidene-myo-inositol 1,6:3,4-Di-O-isopropylidene-5-O-p-methoxybenzyl-myo-inositol obtained in Preparation Example 23 (150 mg, 0.39 mmol) was dissolved in toluene (3 ml), CaH$_2$ (41 mg, 0.9 mmol) was added thereto at room temperature and stirred for 20 minutes. Carbonyldiimidazole (170 mg, 0.98 mmol) was added thereto, stirred for 36 hours. The resulting mixture was filtered and the filtrate was concentrated. The concentrate was purified using column chromatography to obtain the title compound (184 mg) as a white solid.

m.p.=159-162° C. $^1$H-NMR(CDCl$_3$): δ 1.41, 1.49 (each s, 6H), 3.80 (dd, J=9.5, 2.3 Hz, 2H, H-1 & H-3), 3.83 (s, 3H, OCH$_3$), 3.90 (t, J=Hz, 9.0 Hz, 1H, H-5), 4.05 (t, J=9.3 Hz, 2H, H-4 & H-6), 4.82 (s, 2H, PhCH$_2$), 5.92 (t, J=2.2 Hz, 1H, H-2), 6.91 (dt, J=8.7, 2.9 Hz, 2H, Ph), 7.13 (dd, J=1.54, 0.7 Hz, 1H, imidazole), 7.38 (dt, J=8.65, 2.7 Hz, 2H, Ph) 7.44 (t, J=1.4 Hz, 1H, imidazole), 8.17 (s, 1H, imidazole) MS(FAB) m/z 475 (M$^+$+1)

PREPARATION EXAMPLE 27

1-O-benzoyl-4-O-benzyl-2,3:5,6-di-O-isopropylidene-scyllo-inositol

1-O-benzoyl-2,3:5,6-di-O-isopropylidene-scyllo-inositol obtained in Preparation Example 20 (200 mg, 0.549 mmol), silver oxide (1) (381 mg, 1.64 mmol) and tetrabutyl ammonium iodide (40 mg, 0.109 mmol) were dissolved in CH$_2$Cl$_2$, and then, benzyl bromide (0.19 ml, 1.64 mmol) was added dropwise thereto at room temperature. After 2 hours, the mixture was filtered through celite, and the filtrate was washed with $CH_2Cl_2$. The combined organic layer was dried over $MgSO_4$, concentrated and the concentrate was purified using column chromatography (ethyl acetate:hexane=1:9) to obtain the title compound (200 mg) as a white solid.

m.p.=175-176° C. $^1$H-NMR (CDCl$_3$): δ 1.44, 1.46 (each s, 6H), 3.81-3.9 (m, 5H), 4.86 (s, 2H), 5.58 (app. t, J=9.3 Hz, 1H), 7.25-7.56 (m, 7H), 8.06 (d, J=8.7 Hz, 2H) MS (FAB) m/z 478 (M$^+$+Na)

PREPARATION EXAMPLE 28

1-O-benzyl-2,3:5,6-di-O-isopropylidene-scyllo-inositol [Compound of Formula (XII)]

1-O-benzoyl-4-O-benzyl-2,3:5,6-di-O-isopropylidene-scyllo-inositol obtained in Preparation Example 27 (200 mg, 0.44 mmol) was dissolved in $CH_3OH$ (15 ml), NaOCH$_3$ (0.04 ml, 0.17 mmol, 25% w/v in $CH_3OH$) was added dropwise thereto and refluxed for 3 hours. The resulting solution was cooled to room temperature and filtered through silica gel, and the filtrate was concentrated. The residue was washed with 5% ethyl acetate in hexane to remove the methyl benzoate. The title compound (150 mg) was obtained as a white solid.

m.p.=215-216° C. $^1$H-NMR (CDCl$_3$): δ 1.46 (s, 12H), 2.41 (d, J=2.7 Hz, 1H), 3.63 (t, J=9.1 Hz, 4H), 3.71 (t, J=9 Hz, 4H), 3.87 (t, J=8.9 Hz, 1H), 4.1 (app. t, J=9.1 Hz, 1H), 4.83 (s, 2H), 7.26-7.39 (m, 5H) MS (FAB) m/z 373 (M$^+$+Na)

PREPARATION EXAMPLE 29

1-O-p-methoxybenzyl-2,3:5,6-di-O-isopropylidene-scyllo-inositol [Compound of Formula (XI)]

1-O-benzoyl-2,3:5,6-di-O-isopropylidene-scyllo-inositol prepared in Preparation Example 20 (300 mg, 0.85 mmol) was dissolved in dimethylformamide (10 ml), NaH (57.8 mg, 60% in mineral oil, 1.44 mmol) was added thereto at 0° C. After 20 minutes, p-methoxybenzyl chloride (0.12 ml, 0.93 mmol) was added dropwise to the reaction mixture at 0° C. and then a catalytic amount of tetrabutylammonium iodide was added. Reaction mixture was stirred at room temperature for 4 hours and saturated NaHCO$_3$ (50 ml) was added to terminate the reaction. The resulting mixture was extracted with ethyl acetate and the extract was washed with water and brine. The organic layer was dried over MgSO$_4$, concentrated. The crude product was dissolved in CH$_3$OH (15 ml), and NaOCH$_3$ (0.05 ml, 0.057 mmol, 25% w/v in CH$_3$OH) was added. The resulting mixture was refluxed for 3 hours, cooled to room temperature, and filtered through silica gel. The filtrate was combined and concentrated and the resulting residue was purified using column chromatography (ethyl acetate hexane=1:3) to obtain the title compound (210 mg).

m.p.=198-200° C. $^1$H-NMR (CDCl$_3$): δ 1.47 (s, 12H), 2.41(brs, 1H), 3.59-3.63 (m, 5H), 3.65 (s, 3H), 3.80 (app. t, J=9.1 Hz, 1H), 4.76 (s, 2H), 6.87 (d, J=9 Hz, 2H), 7.33 (d, J=9.1 Hz, 2H) MS (FAB) m/z 403 (M$^+$+Na)

PREPARATION EXAMPLE 30

1-O-benzyl-4-O-(1-imidazolylcarbonyl)-2,3:5,6-di-O-isopropylidene-scyllo-inositol 1-O-benzyl-2,3:5,6-di-O-isopropylidene-scyllo-inositol prepared in Preparation Example 28 (70 mg, 0.19 mmol) was dissolved in toluene (6 ml), CaH$_2$ (21 mg, 0.49 mmol) was added thereto at room temperature for 20 minutes. Then, carbonyldiimidazole (81 mg, 0.49 mmol) was added thereto and stirred for 18 hours. The mixture was filtered and the filtrate was purified using column chromatography (ethyl acetate:hexane=1:1) to obtain the title compound (87 mg) as a white solid.

m.p.=214-216° C. $^1$H-NMR(CDCl$_3$): δ 1.45, 1.47 (each s, 6H), 3.80-3.87 (m, 5H), 4.85 (s, 2H, PhCH$_2$), 5.45 (app.t, J=1.9 Hz, 1H, H-1), 7.07 (s, 1H), 7.29-7.42 (m, 6H), 8.16 (s, 1H) MS(FAB) m/z 445(M$^+$+1), 467(M$^+$+Na)

PREPARATION EXAMPLE 31

4-O-allyl-2,3:5,6-di-O-isopropylidene-scyllo-inositol

1-O-benzoyl-2,3:5,6-di-O-isopropylidene-scyllo-inositol obtained in Preparation Example 20 (500 mg, 1.37 mmol) was dissolved in dimethylformamide (10 ml), NaH (9.8 mg, 60% in mineral oil, 2.47 mmol) was added thereto at 0° C. After 10 minutes, allyl bromide (0.18 ml, 2.05 mmol) was added thereto, followed by stirring the mixture at room temperature for 20 hours. Thereafter, the reaction mixture was diluted with water (50 ml) and resultant was extracted using ethyl acetate. The organic layer was washed with water and saturated NaCl, dried over MgSO$_4$ and concentrated. The concentrate was purified using column chromatography (ethyl acetate:hexane=3:7) to obtain 4-O-allyl-1-O-benzoyl-2,3:5,6-di-O-isopropylidene-scyllo-inositol (450 mg).

The obtained 4-O-allyl-1-O-benzoyl-2,3:5,6-di-O-isopropylidene-scyllo-inositol (400 mg, 0.989 mmol) was dissolved in CH$_3$OH (12 ml), NaOCH$_3$ (0.09 ml, 0.395 mmol, 25% w/v in CH$_3$OH) was added thereto dropwise and refluxed for 3 hours. Thereafter the resulting solution was cooled to room temperature, filtered through silica gel, and the filtrate was concentrated. The residue was washed with 5% ethyl acetate in hexane to remove the methyl benzoate. The title compound was obtained as a white solid (290 mg).

m.p.=200-202° C. $^1$H-NMR (CDCl$_3$): δ 1.46 (s, 12H), 2.46 (d, J=2.7 Hz, 1H), 3.57-3.68 (m, 4H), 3.83 (t, J=8.1 Hz, 1H), 4.05 (t, J=6.9 Hz, 1H), 4.28 (d, J=5.7 Hz, 2H), 5.21 (d, J=10.2 Hz, 1H), 5.33 (dd, J=18.1 Hz, 1.5 Hz 1H), 5.95 (m, 1H) MS (FAB) m/z 301 (M$^+$+1), 323 (M$^+$+Na)

PREPARATION EXAMPLE 32

4-O-(N,N-dibenzyl-2'-aminoethyl)-2,3:5,6-di-O-isopropylidene-scyllo-inositol

4-O-allyl-2,3:5,6-di-O-isopropylidene-scyllo-inositol obtained in Preparation Example 31 (250 mg, 0.832 mmol) and NaHCO$_3$ (139 mg, 1.66 mmol) were dissolved in the mixture of CH$_2$Cl$_2$ and CH$_3$OH (6:1, 50 ml). Ozone was passed slowly thereto at −78° C. until the color of the solution turned to deep blue. Thereafter, N$_2$ was bubbled thereto until the blue color of the solution disappeared. Triphenylphosphine (327 mg, 12.49 mmol) was added to the solution and stirred at room temperature for 12 hours. After completion of the reduction reaction of hydroperoxide, the mixture was purified using column chromatography to obtain 4-O-ethanal-2,3:5,6-di-O-isopropylidene-scyllo-inositol (235 mg). The compound 4-O-ethanal-2,3:5,6-di-O-isopropylidene-scyllo-inositol (150 mg, 0.496 mmol) was dissolved in dichloroethane (15 ml), and dibenzylamine (0.04 ml, 0.744 mmol) was added at 0-5° C. After 10 minutes, sodium triacetoxyborohydride (265 mg, 1.24 mmol) were added thereto, and the resulting mixture was stirred at 0-5° C. for 1 hours and then continued for 12 hours at room temperature. After completion of the reaction, the mixture was extracted with $CH_2Cl_2$ (60 ml), the extract was washed with saturated $NaHCO_3$, water, and brine. The organic layer was dried over $MgSO_4$, concentrated and the residue was purified by column chromatography (ethyl acetate:hexane=1:1) to obtain the title compound (180 mg) as a white solid.

m.p.=144-145° C. $^1$H-NMR (CDCl$_3$): δ 1.44 (s, 12H), 2.70 (brs, 1H), 2.74 (t, J=6 Hz, 2H), 3.54-3.59 (m, 4H), 3.64 (s, 4H), 3.74 (t, J=6.2 Hz, 1H), 3.87 (t, J=6.2 Hz, 2H), 4.0 (t, J=6.3 Hz, 1H), 7.19-7.39 (m, 10H) MS (FAB) m/z 484 (M$^+$+1), 506 (M$^+$+Na)

PREPARATION EXAMPLE 33

4-O-(N,N-dibenzyl-2'-aminoethyl)-1-O-(methyloxycarbonylmethyl)-2,3:5,6-di-O-isopropylidene-scyllo-inositol [Compound of Formula (XIII)]

4-O-(N,N-dibenzyl-2'-aminoethyl)-2,3:5,6-di-O-isopropylidene-scyllo-inositol obtained in Preparation Example 32 (125 mg, 0.258 mmol) was dissolved in dimethylformamide (10 ml), Ag$_2$O (119 mg, 0.517 mmol), methyl bromoacetate (50 μl, 0.517 mmol) and a catalytic amount of tetrabutylammonium iodide were added sequentially to the reaction mixture. After stirring for 12 hours at room temperature the reaction mixture was filtered through celite and the filtrate was concentrated and purified using column chromatography (ethyl acetate:hexane=1:2) to obtain the title compound (127 mg) as a white solid.

m.p.=130-132° C. $^1$H-NMR (CDCl$_3$): δ 1.41 (s, 12H), 2.72 (t, J=6 Hz, 2H), 3.58 (t, J=6.3 Hz, 2H), 3.63-3.89 (m, 13H), 4.36 (s, 2H), 7.12-7.40 (m, 10H) MS (FAB) m/z 556 (M$^+$+1), 579 (M$^+$+Na)

PREPARATION EXAMPLE 34

4-O-(2-aminoethyl)-1-O-(methyloxycarbonylmethyl)-2,3:5,6-di-O-isopropylidene-scyllo-inositol 4-O-(N,N-dibenzyl-2'-aminoethyl)-1-O-(methyloxycarbonylmethyl)-2,3:5,6-di-O-isopropylidene-scyllo-inositol obtained in Preparation Example 33 (20 mg, 0.035 mmol) was dissolved in the mixture of $CH_2Cl_2$ and methanol (1:2, 12 ml), palladium hydroxide (20% on carbon, 9.7 mg) was added thereto, followed by stirring the mixture under H$_2$ (40 psi) for 2 hours. Thereafter, reaction mixture was filtered through celite and the filtrate was concentrated. The product was crystallized from methanol to obtain the title compound (14 mg) as a white solid.

m.p.=193-195° C. $^1$H-NMR (CD$_3$OD): δ 1.41 (s, 12H), 3.10 (t, J=6.0 Hz, 2H), 3.27 (dd, J=6.5, 1.8 Hz, 2H), 3.69-3.90 (m, 11H), 4.28 (s, 2H) MS (FAB) m/z 376 (M$^+$+1)

PREPARATION EXAMPLE 35

4-O-(N,N-dibenzyl-2'-aminoethyl)-1-O-(carboxymethyl)-2,3:5,6-di-O-isoproylidene-scyllo-inositol 4-O-(N,N-dibenzyl-2'-aminoethyl)-1-O-(methyloxycarbonylmethyl)-2,3:5,6-di-O-isopropylidene-scyllo-inositol obtained in Preparation Example 33 (20 mg, 0.035 mmol) was dissolved in methanol (3 ml), NaOH pellet (4.3 mg, 0.107 mmol) was added thereto, followed by stirring the mixture at room temperature for 10 hours. The mixture was concentrated, and diluted with water (5 ml). The aqueous layer was washed with diethyl ether (2×2 ml), and 5% aq. AcOH was added dropwise to the solution to adjust the pH ~6.5. Then, the aqueous layer was extracted with $CH_2Cl_2$ (4×4 ml) and the combined organic layer was dried over $Na_2SO_4$ and concentrated. The title compound was obtained as a white solid (13 mg).

$^1$H-NMR (CDCl$_3$): δ 1.41 & 1.44 (each s, 6H), 2.77 (t, J=5.8 Hz, 2H), 3.35-3.91 (m, 12H), 4.37 (s, 2H), 7.20-7.40 (m, 10H) MS (FAB) m/z 542 (M$^+$+1), 564 (M$^+$+Na)

EXAMPLE 1

Preparation of the Compound of Formula (II)
(Wherein X=—O—CO—O— and n=5)

1-1) Preparation of Myo-Inositol Dimer

The compound obtained in Preparation Example 21 (1.62 g, 3.4 mmol) was dissolved in toluene (21 ml), the compound obtained in Preparation Example 5 (1.8 g, 5 mmol) and 1,8-diazobicyclo[5.4.0]undec-7-ene (0.05 ml, 0.34 mmol) were added thereto, and the mixture was stirred at room temperature for 18 hours. The resulting solution was extracted with $CH_2Cl_2$, the extract was dried over MgSO$_4$ and concentrated under a reduced pressure. The concentrate was purified by crystallization from hexane/ethyl acetate (5:1) to obtain the coupled dimeric compound (2.23 g) as a white solid.

m.p.=225-226° C. $^1$H-NMR (CDCl$_3$): 1.10-1.72 (m, 24H), 3.35&3.36 (dd, J=9.3 Hz, 11.0&9.5 Hz, 11.1 Hz, 2H), 3.49 (t, J=9.3&10.8 Hz, 2H), 3.73 (dd & t, J=2.6 Hz, 5.8&1.4 Hz, 2H), 4.00-4.15 (m, 6H), 4.12 (dd, J=5.9 Hz, 9.1&2.6 Hz, 5.9 Hz, 4H), 4.69 (t, J=2.5&4.4 Hz, 4H), 4.82 (s, 8H), 4.95&4.96 (dd, J=4.1 Hz, 10.5&4.1 Hz, 10.5 Hz, 2H), 5.04&5.05 (dd, J=6.9 Hz, 11.1&7.0 Hz, 11.0 Hz, 2H), 6.89 (d, J=8.7 Hz, 4H), 7.24-7.42 (m, 14H) IR (KBr): 1748 cm$^{-1}$ (CO) MS (FAB) m/z 779.82 (M$^+$+Na)

1-2) Removal of Acetonide Protecting Group from the Myo-Inositol Dimer

Myo-inositol dimer obtained in Example 1-1) (2.21 g) was dissolved in $CH_2Cl_2$ (25 ml), and then, CH$_3$OH (24.3 ml) and p-toluenesulfonic acid (286.1 mg, 1.46 mmol) were added thereto, followed by stirring the mixture at room temperature for 14 hours. The resultant was filtered to obtain the myo-inositol dimer having no acetonide group (1.45 g) as a white solid.

m.p.=169° C. $^1$H-NMR (DMSO): 3.11-3.24 (m, 4H), 3.35-3.48 (m, 5H), 3.49 (dd, J=9.6 Hz, 21.2 Hz, 4H), 3.74 (s, 3H), 3.90-3.97 (m, 3H), 4.25-4.33 (m, 2H), 4.53 (dd, J=1.8 Hz, 24.9 Hz, 4H), 4.70-4.74 (m, 12H), 4.77-4.81 (m, 2H), 6.89 (d, J=8.6 Hz, 2H), 7.21-7.35 (m, 5H), 7.43 (d, J=7.1 Hz, 2H) MS (FAB) m/z 619 (M$^+$+Na)

1-3) Introduction of Amino Acid to the Myo-Inositol Dimer by Acylation

The compound obtained in Example 1-2) (200 mg, 0.34 mmol), the compound obtained in Preparation Example 8 (1.55 g, 6.7 mmol) and N,N-dimethylaminopyridine (62.3 mg, 0.51 mmol) were dissolved in dimethylformamide (4 ml), and then, 1-[3-(dimethylamino)propyl]-ethylcarbodiimide hydrochloride (1.3 g, 6.7 mmol) was added thereto, followed by stirring the mixture at room temperature for a day. After completion of the reaction, the mixture was extracted from $CH_2Cl_2$ and the extract was washed with saturated NaHCO$_3$ and water. The organic layer was dried over Na$_2$SO$_4$ and concentrated to obtain the title compound having eight (8) amino acid residues (776.6 mg) as a brown solid.

$^1$H-NMR (CDCl$_3$): 1.13-1.32 (m, 16H), 1.36 (s, 72H), 1.45-1.57 (m, 32H), 2.06-2.15 (m, 16H), 2.95-3.02 (m, 16H), 3.7 (s, 3H), 3.85-3.91 (m, 1H), 4.22 (dd, J=1.9 Hz, 9.3 Hz, 1H), 4.48 (d, J=11.8 Hz, 2H), 4.55 (d, J=6.6 Hz, 2H), 4.60-5.68 (m, 10H), 6.76 (d, J=8.7 Hz, 2H), 7.05 (d, J=8.4 Hz, 2H), 7.10-7.26 (m, 5H) MS (FAB) m/z 2324.6 (M$^+$+Na)

1-4) Removal of p-methoxybenzyl Protecting Group

The compound obtained in Example 1-3) (705.1 mg, 0.31 mmol) was dissolved in $CH_2Cl_2/H_2O$ (18:1) (5 ml) and cooled to 0° C. Then, 2,3-dichloro-5,6-dicyano-1,4-benzoquinone (139.0 mg, 0.61 mmol) was added thereto and the mixture was stirred at room temperature. After 2 days, saturated $NaHCO_3$ was added to terminate the reaction and the resultant was washed with water. The organic layer was dried over $Na_2SO_4$, and concentrated to obtain the title compound having no p-methoxybenzyl protecting group (373.9 mg) as a brown solid.

$^1$H-NMR (CDCl$_3$): 1.17-1.26 (m, 16H), 1.37 (s, 72H), 1.41-1:53 (m, 32H), 2.94-3.05 (m, 16H), 2.07-2.41 (m, 16H), 3.86-3.92 (m, 2H), 4.31-5.56 (m, 24H), 7.11-7.27 (m, 5H) MS (FAB) m/z 2204.8 (M$^+$+Na)

1-5) Introduction of Fluorescent Tag

The compound obtained in Example 1-4) (284.1 mg, 0.13 mmol) and N,N-dimethylaminopyridine (47.6 mg, 0.38 mmol) were dissolved in acetonitrile (4 ml), and then, 5-dimethylamino-1-naphthalenesulfonyl chloride (70.2 mg, 0.26 mmol) was added thereto, followed by stirring the mixture at room temperature. After 2 days, saturated $NH_4Cl$ (8.3 ml) was added thereto and the resultant was extracted from ethyl acetate. The extract was washed with saturated NaCl, dried over $Na_2SO_4$, concentrated and purified using column chromatography (ethyl acetate:hexane=1:1) to obtain the title compound having an introduced fluorescent tag (261.7 mg) as a yellow solid.

$^1$H-NMR (CDCl$_3$): 1.21 (s, 16H), 1.38 (s, 72H), 1.53-1.59 (m, 32H), 1.99-2.33 (m, 16H), 2.83 (s, 6H), 2.94-3.04 (m, 16H), 3.89(t, J=9.8 Hz, 1H), 4.56 (dd, J=12.0 Hz, 18.6 Hz, 2H), 4.69-5.54 (m, 11H), 7.11-7.29 (m, 6H), 7.50 (dd, J=8.4 Hz, 16.5 Hz, 2H), 8.03 (d, J=7.5 Hz, 1H), 8.18 (d, J=7.2 Hz, 1H), 8.61 (brs, 1H) MS (FAB) m/z 2438.1 (M$^+$+Na)

1-6) Removal of t-Boc Protecting Group at the Amino Acid N-Terminal

The compound obtained in Example 1-5) (202.3 mg, 0.08 mmol) was dissolved in ethyl acetate saturated with HCl (8 ml). The mixture was stirred at room temperature for 45 minutes and the solvent was removed under a reduced pressure, to obtain the title compound having no t-Boc protecting group at the amino acid N-terminal (180.4 mg) as a yellow solid.

$^1$H-NMR (CD$_3$OD): 1.37 (m, 16H), 1.69 (m, 32H), 2.23 (m, 16H), 2.94 (m, 16H), 3.28-3.30 (m, 1H), 3.44 (s, 6H), 4.71 (m, 2H), 4.95-5.62 (m, 11H), 7.21-7.30 (m, 5H), 7.87-7.98 (m, 2H), 8.14 (brs, 1H), 8.53 (dd, J=8.4 Hz, 15.0 Hz, 2H), 8.95 (t, J=3.9 Hz, 1H) MS (MALDI-TOF) m/z 1636.2 (M$^+$+Na)

1-7) Introduction of Guanidinium Group at the Amino Acid N-Terminal

The compound obtained in Example 1-6) (141.6 mg, 0.07 mmol) was dissolved in dimethylformamide (2.8 ml), and triethylamine (0.4 ml, 3 mmol) and N,N-di-Boc-N'-trifluoromethanesulfonylguanidine (1.2 g, 3 mmol) obtained in Preparation Example 11 were added thereto, followed by stirring the mixture at room temperature. After 2 days, ethyl acetate was added thereto, and the mixture was washed successively with 2N $NaHSO_4$, saturated $NaHCO_3$ and NaCl solutions. The organic layer was dried over $Na_2SO_4$, concentrated and purified using column chromatography (ethyl acetate:hexane=1:2) to obtain the title compound having eight (8) guanidinium groups (93.1 mg) as a yellow solid.

$^1$H-NMR (CDCl$_3$): 1.13-1.65 (m, 192H), 1.60-2.31 (m, 16H), 2.82 (s, 6H), 3.24-3.36 (m, 16H), 3.88 (t, J=9.9 Hz, 1H), 4.56-5.51 (m, 13H), 7.11-7.29 (m, 6H), 7.51 (dd, J=8.4 Hz, 16.2 Hz, 2H), 7.99 (d, J=8.7 Hz, 1H), 8.17 (dd, J=0.9 Hz, 7.5 Hz, 1H), 8.22-8.28 (m, 8H), 11.46 (s, 8H)

1-8) Removal of t-Boc Protecting Group at Guanidinium Terminal

The compound obtained in Example 1-7) (38 mg, 0.01 mmol) was dissolved in trifluoroacetic acid/CH$_2$Cl$_2$ (1:1) (2 ml), stirred at room temperature for 5 hours. The mixture was concentrated under a reduced pressure and water and ethyl acetate were added thereto. The aqueous layer was separated, collected and lyophilized to obtain the title compound having no t-Boc protecting group at guanidinium terminal (27 mg) as a yellow solid.

$^1$H-NMR (CD$_3$OD): 1.13-1.35 (m, 16H), 1.42-1.61 (m, 32H), 2.13-2.43 (m, 16H), 2.88 (s, 6H), 3.02-3.16 (m, 16H), 4.01 (t, J=9.6H, 1H), 4.64 (dd, J=11.9 Hz, 18.7 Hz, 2H), 5.01-5.61 (m, 11H), 7.16-7.28 (m, 6H), 7.52-7.66 (m, 2H), 8.00 (d, J=8.6 Hz, 1H), 8.27 (d, J=7.3 Hz, 1H), 8.64 (d, J=8.5 Hz, 1H) MS (MALDI-TOF) m/z 1973.1 (M$^+$+Na)

1-9) Removal of benzyl (Bn) Protecting Group

The compound obtained in Example 1-8) (10 mg, 3.5 µmol) was dissolved in methanol (1 ml), palladium hydroxide (20% on carbon, 20 mg) was added thereto, followed by stirring the mixture under the presence of 1 atm of H$_2$ for 4 hours. The mixture was filtered through celite and the filtrate was concentrated under a reduced pressure to obtain the title compound having no benzyl protecting group (7 mg) as a yellow solid.

$^1$H-NMR (CD$_3$OD): 1.1-1.6 (m, 48H), 2.1-2.5 (m, 16H), 2.90 (s, 6H), 3.0-3.26 (m, 16H), 3.97 (t, J=9.9 Hz, 1H), 5.0-5.7 (m, 11H), 7.29 (d, J=7.7 Hz, 1H), 7.57 (t, J=8.1 Hz, 1H), 7.67 (t, J=8.1 Hz, 1H), 8.00 (d, J=8.5 Hz, 1H), 8.30 (d, J=7.5 Hz, 1H), 8.64 (d, J=8.7 Hz, 1H)

EXAMPLE 2

Preparation of the Compounds of Formula (II) (wherein X=—O—CO—O—, n=3 and n=7)

The compounds of formula (II) wherein n=3 and n=4 were similarly prepared in accordance with Example 1 employing 4-Boc-aminobutanoic acid and 8-Boc-aminooctanoic acid obtained in Preparation Examples 7 and 9, respectively, instead of 6-Boc-aminohexanoic acid as in Example 1-3).

EXAMPLE 3

Preparation of the Compound of Formula (III) (Wherein X=—O—CO—O—)

3-1) The compound obtained in Preparation Example 25 (42 mg, 0.12 mmol) was dissolved in tetrahydrofuran (5 ml), NaH (6 mg, 0.25 mmol) was added thereto at 0° C. and warmed to room temperature, followed by stirring the mixture for 25 minutes. Then, the mixture was cooled to 0° C. and the compound obtained in Preparation Example 26 (48 mg, 0.10 mmol) was added thereto, and stirred for 2 hours. The resulting solution was diluted with ethyl acetate (30 ml) and washed with saturated NaHCO$_3$ (30 ml) and brine. The organic layer was dried over Na$_2$SO$_4$, concentrated and purified using column chromatography to obtain the coupled dimeric compound (29 mg).

m.p.=168-170° C. $^1$H-NMR(CDCl$_3$): δ 1.45, 1.46 (each s, 12H), 3.68 (app dt, J=9.5, 2.1 Hz, 4H, H-1, H-1', H-3, H3'), 3.82 (s, 3H, OCH$_3$), 3.82 (t, J=9.1, 1H, H-5'), 4.10 (t, J=9.3 Hz, 2H, H-4' & H-6'), 4.23 (t, J=9.6 Hz, 2H, H-4 & H-6), 4.39 (t, J=1.8 Hz, 1H), 4.79, 4.85 (2s, 4H, 2PhCH$_2$), 5.17 (t, J=9.6 Hz, H-5), 5.58 (t, J=2.0 Hz, H-2'), 6.89 (dd, J=6.7, 1.9 Hz, 2H, Ph), 7.28-7.40 (m, 8H, Ph) MS (FAB) m/z 779(M$^+$+Na)

3-2) Amino acids were introduced to the dimeric compound by acylation and guanidine group were introduced to the amino acid N-terminals of the dimer in accordance with Example 1 to obtain the compound of formula (III).

EXAMPLE 4

Preparation of the Compound of Formula (IV) (Wherein X=—O—CO—O—)

4-1) The compound obtained in Preparation Example 29 (43 mg, 0.11 mmol) was dissolved in tetrahydrofuran (2 ml), NaH (1.2 mg, 0.05 mmol) was added thereto at 0° C. and warmed to room temperature, followed by stirring the mixture for 15 minutes. The mixture was added to the solution of the compound obtained in Preparation Example 30 (50 mg, 0.11 mmol) in tetrahydrofuran (3 ml) at 0° C., stirred at 0~5° C. for 1.5 hours and diluted with CH$_2$Cl$_2$(25 ml). The resultant was washed with saturated NH$_4$CO$_3$ (30 ml) and the organic layer was dried over MgSO$_4$, concentrated and purified using column chromatography (ethyl acetate:hexane=1:3) to obtain the coupled dimeric compound (41 mg).

m.p.=284-286° C. $^1$H-NMR(CDCl$_3$): δ 1.43, 1.47 (each s, 12H), 3.66-3.88 (m, 13H), 4.47 (s, 2H), 4.83 (s, 2H), 5.12 (t, J=9.3 Hz, 2H, H-6, H-6'), 6.88 (d, J=8.7 Hz, 2H), 7.27-7.42 (m, 7H) MS (FAB) m/z 757(M$^+$+1), 780(M$^+$+Na)

4-2) Amino acids were introduced to the dimeric compound by acylation and guanidine groups were introduced to the amino acid N-terminals of the dimer in accordance with Example 1 to obtain the compound of formula (IV) wherein X=—O—CO—O—.

EXAMPLE 5

Preparation of formula (IV) (wherein X=—O—CH$_2$—CO—NH—(CH$_2$)$_2$—O—)

5-1) The compound obtained in Preparation Example 34 (8.3 mg, 0.022 mmol) and the compound obtained in Preparation Example 35 (12 mg, 0.022 mmol) were dissolved in dimethylformamide (2.5 ml), and then, triethylamine (3 μl, 0.035 mmol), 1-hydroxybenzotriazole hydrate (HOBT; 3.2 mg, 0.024 mmol) and 1-[3-(dimethylamino)propyl]-ethylcarbodiimide hydrochloride (4.6 mg, 0.024 mmol) were successively added thereto at room temperature and the resulting mixture was stirred for 22 hours. The mixture was diluted with ethyl acetate (15 ml) and the organic layer was washed with NH$_4$Cl (5 ml), saturated NaHCO$_3$ (10 ml×2) and distilled water (5 ml×3). The organic layer was dried over Na$_2$SO$_4$, concentrated and purified using column chromatography (ethyl acetate:hexane=1:1) to obtain the coupled dimeric compound (14 mg) as a white solid.

$^1$H-NMR(CDCl$_3$): δ 1.40, 1.43 (each s, 6H), 2.72 (t, J=6.1 Hz, 2H), 3.35-3.88 (m, 25H), 4.23 (s, 2H), 4.36 (s, 2H), 7.02 (t, J=6 Hz, 1H), 7.19-7.39 (m, 10H) MS (FAB) m/z 899(M$^+$+1), 921(M$^+$+Na)

5-2) Amino acids were introduced to the dimeric compound by acylation and guanidine groups were introduced to the amino acid N-terminals of the dimer in accordance with Example 1 to obtain the compound of formula (IV) wherein X=—O—CH$_2$—CO—NH—(CH$_2$)$_2$—.

Test Example 1

Measurement of Uptake into Cytoplasm

The permeability through the plasma membrane of each of the compounds having dansyl fluorescent tag prepared in the above examples was measured and compared with that of arginine nonamer (Arg$_9$) which is known to efficiently cross a biological membrane, and that of the intermediate prepared in Example 1-6) having no guanidine group as a control.

First, a cover glass was placed on a C12 well plate and COS 7 cells (monkey kidney epithelial cell) were cultured thereon. The medium was DMEM (Dulbecco's modified Eagle's medium) containing 10% FBS, and the cells were stabilized for 24 hours before culturing on a serum-free medium for 24 hours to starve the cells. Thereafter, the cells were treated with dansyl-Arg$_9$, the intermediate prepared in Example 1-6), or one of the compounds prepared in Examples 1 and 2 at a concentration of ~7 μM for 5 minutes, the cover glass was taken out, washed with PBS and mounted on a slide. A section of the collected surface was observed with a confocal microscope equipped with Ar laser (455 nm) to detect the fluorescent tag at a magnification ×400 (objective len's 40× and ocular lens 10×). The results are shown in FIG. 1.

FIG. 1 shows the fluorescent images of COS 7 cell slides treated with dansyl-Arg$_9$ (1); the intermediate prepared in Example 1-6) having no guanidine groups (2); and the compounds of formula (II) in accordance with the present invention (wherein n=3, 5 and 7), respectively (3 to 5). The green fluorescent color shows the intensity of the emission by the permeated compound inside cells.

As shown in FIG. 1, the compounds according to the present invention (3 to 5) show a higher permeability than d-Arg$_9$ (1), and the intermediate having no guanidine groups fails to permeate into the cell. Among the inventive compounds, the compound having the n value of 5 (4) shows the highest permeability.

Test Example 2

Measurement of Uptake into Nucleus

The permeability through the nuclear membrane of each of the compounds having dansyl fluorescent tag prepared in the above examples was measured and compared with that of arginine nonamer (Arg$_9$) which is known to be highly permeable through a biological membrane, and also with that of the intermediate prepared in Example 1-6) having no guanidine groups.

First, a cover glass was placed on a C12 well plate and mouse macrophage RAW264.7 cells were cultured thereon. The medium was DMEM (Dulbecco's modified Eagle's medium) containing 10% FBS, and the cells were stabilized for 24 hours before culturing on a serum-free medium for 24 hours to starve the cells. Thereafter, the cells were treated with RNase (100 μg/ml) at room temperature, and then, treated with propidium iodide (2 μg/ml) at a constant temperature of 23 to 25° C. for 5 minutes to dye nucleus, followed by treating the cells with PBS 3 times. Then, the cells were treated with dansyl-Arg$_9$, the intermediate prepared in Example 1-6), or one of the compounds prepared in Examples 1 and 2 at a concentration of ~7 μM for 5 minutes, the cover glass was taken out, washed with PBS and mounted on a slide. A section of the collected surface was observed with a confocal microscope equipped with Ar laser (455 nm) to detect the fluorescent tag at a magnification of ×400 (objective lens 40× and ocular lens 10×). The results are shown in FIG. 2.

Figure 2:
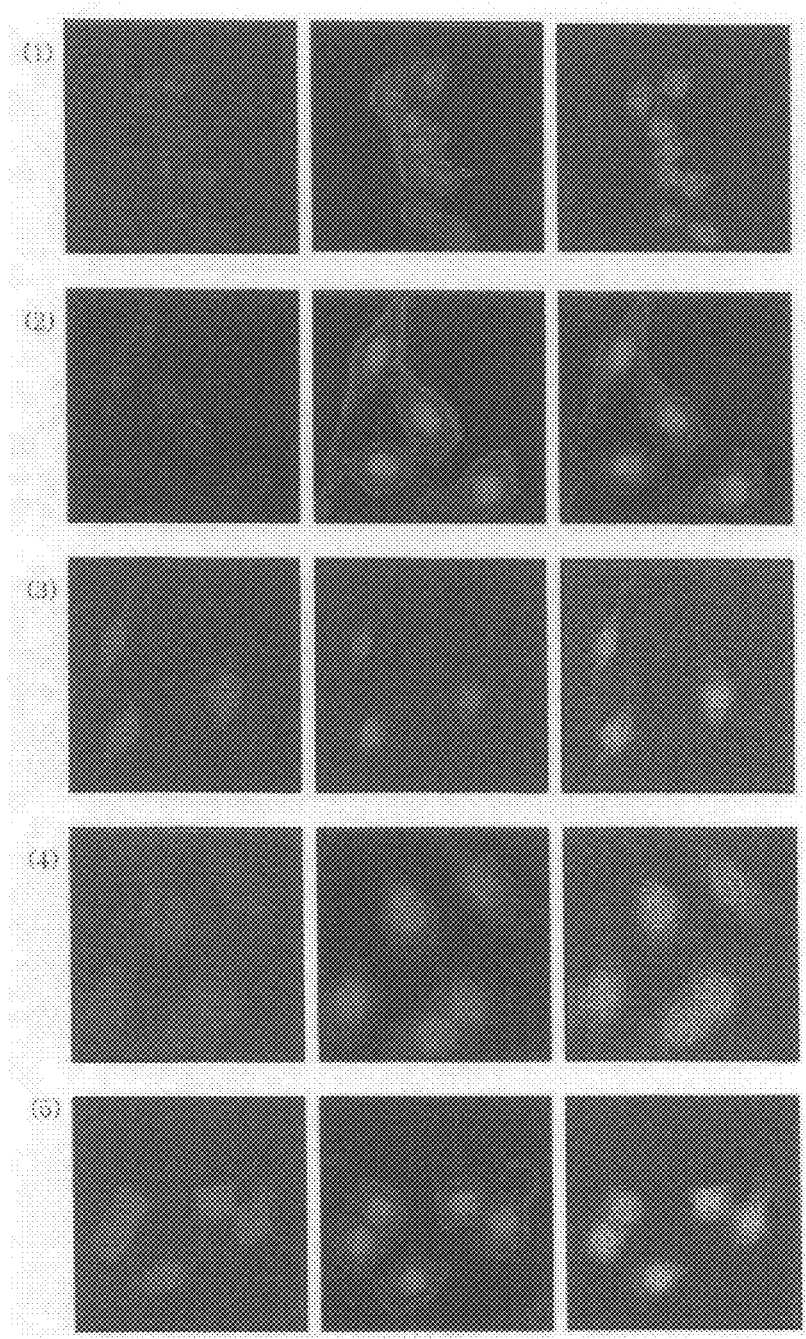
FIG. 2 presents comparative degrees of nuclear membrane transmission of a various compounds, dansyl-$Arg_9$ (1), the intermediate prepared in Example 1-6) having no guanidinium group (2), and the inositol derivatives in accordance with Examples 1 and 2 of the present invention (3 to 5).

FIG. 2 shows the fluorescent images of RAW264.7 cell slides treated with dansyl-$Arg_9$ (1); the intermediate prepared in Example 1-6) having no guanidine groups (2); and the compounds of formula (II) in accordance with the present invention (wherein n=3, 5 and 7), respectively (3) to (5). The green color of the left first column shows the intensity of the fluorescence emitted by the permeated compound in cells, the red color of the middle column shows the amount of the dyed nucleus with propidium iodide, and the right column show the merged color between green and red, where the intense yellow color indicates compounds present in the nucleus.

As shown in FIG. 2, the compounds according to the present invention (3 to 5) show a higher permeability into the nucleus than d-$Arg_9$ (1). Among the inventive compounds, the compounds having an n value of 3(3) and 7(5) show a higher permeability.

Further, ionic complex formulation comprising a mixture of a compound of formulae (II) to (IV) without a fluorescent marker in accordance with the present invention and the myo-inositol phosphate having a fluorescent tag described in [Prestwich, G. D., Acc. Chem. Res., 29, 503 (1996); Chung S. K. et al. J. Org. Chem., 67, 5256 (2002)] also shows high permeability into cells.

While the invention has been described with respect to the above specific embodiments, it should be recognized that various modifications and changes may be made to the invention by those skilled in the art which also fall within the scope of the invention as defined by the appended claims.

What is claimed is:

1. An inositol derivative of formula (I):

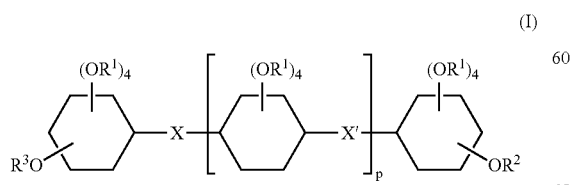

wherein $R^1$ is

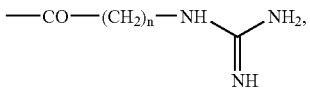

where n is an integer in the range of 1 to 12;

$R^2$ and $R^3$ are each independently H, alkyl, arylalkyl, cycloalkyl, heteroalkyl, —$(CH_2)_m$NHR', —$(CH_2)_l$CO$_2$R'', —COR''' or —SO$_2$R'''', where R', R'', R''' and R'''' are each alkyl, m is an integer in the range of 2 to 5, and 1 is an integer in the range of 1 to 5;

p is an integer in the range of 0 to 2; and

X and X' are each independently —O—CO—O—, —O—CO—NH—$(CH_2)_m$—O—, —O—CO—$(CH_2)_1$—O— or —O—$(CH_2)_1$—CO—NH—$(CH_2)_m$—O—, where m and 1 are the same as defined above.

2. The inositol derivative of claim 1, which is represented by formula (XV):

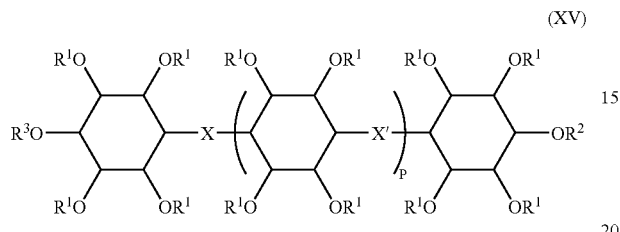

(XV)

wherein $R^1$, $R^2$, $R^3$, X, X' and p are the same as defined in claim 1.

3. The inositol derivative of claim 1, wherein p is 0 or 1.

4. The inositol derivative of claim 1, wherein n is an integer in the range of 3 to 8.

5. The inositol derivative of claim 1, which is represented by formula (II), (III) or (IV):

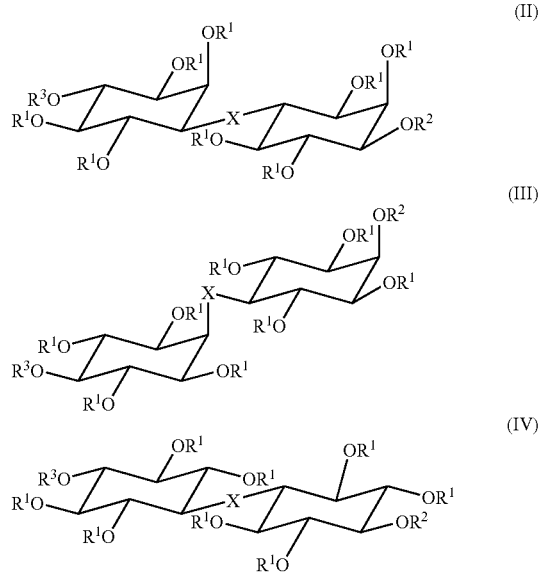

(II)

(III)

(IV)

wherein $R^1$, $R^2$, $R^3$ and X are the same as defined in claim 1.

6. A method for preparing inositol derivatives of formula (I):

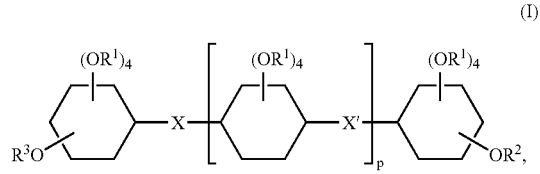

(I)

comprising the steps of:

(a) obtaining intermediates by protecting the hydroxyl groups of myo- or scyllo-inositol;

(b) coupling two or more of the intermediates obtained in step (a) to produce X and/or X' couplings, followed by removal of the protecting groups;

(c) introducing one or more amino acids corresponding to $R^1$ groups to the inositol polymer obtained in step (b) by acylation; and (d) introducing guanidinium groups to the amino acid ($R^1$) N-termini of the inositol polymer so that the amino acids are guanidinylated at the amino groups, wherein $R^1$ is

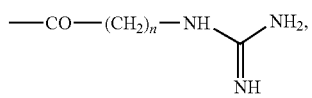

where n is an integer in the range of 1 to 12;

$R^2$ and $R^3$ are each independently H, alkyl, arylalkyl, cycloalkyl, heteroalkyl, —$(CH_2)_m$NHR', —$(CH_2)_1$CO$_2$R'', —COR''' or —SO$_2$R'''', where R', R'', R''' and R'''' are each alkyl, m is an integer in the range of 2 to 5, and 1 is an integer in the range of 1 to 5;

X and X' are each independently —O—CO—O—, —O—CO—NH—$(CH_2)_m$—O—, —O—CO—$(CH_2)_1$—O—, or —O—$(CH_2)_1$—CO—NH—$(CH_2)_m$—O—, where m and 1 are the same as defined above; and p is an integer in the range of 0 to 2.

7. The method of claim 6, wherein the intermediate obtained in step (a) is selected from the compounds represented by formulae (V) to (XIII):

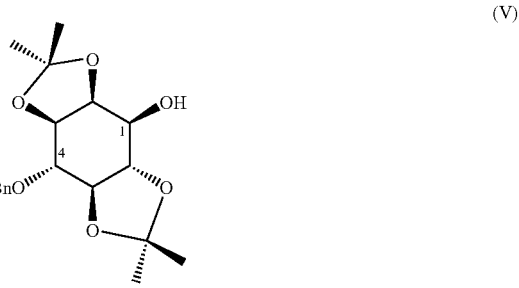

(V)

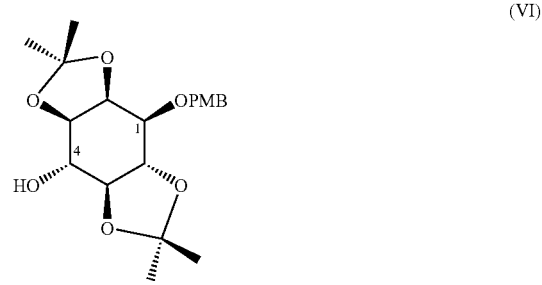

(VI)

-continued

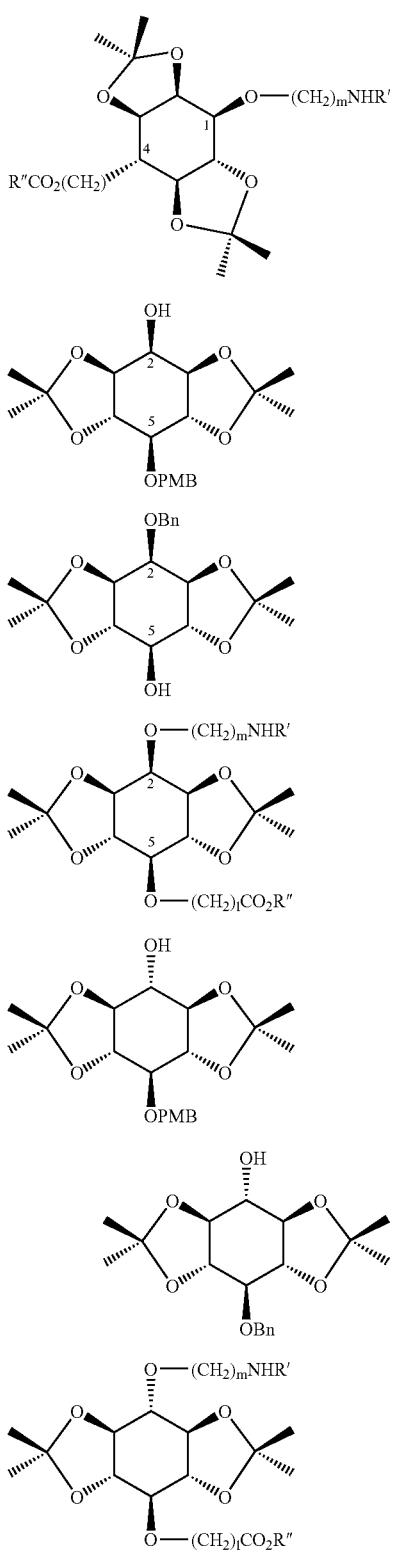

(VII)

(VIII)

(IX)

(X)

(XI)

(XII)

(XIII)

wherein
R', R", are each alkyl,
l is an integer in the range of 1 to 5,
m is an integer in the range of 2 to 5,
Bn is benzyl, and
PMB is p-methoxybenzyl.

8. A composition for delivering a drug or a diagnostic reagent across a biological membrane into a cell, comprising the drug or diagnostic reagent and an inositol derivative of formula (I):

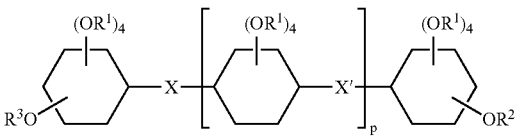

(I)

wherein
$R^1$ is

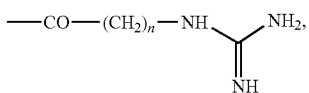

where n is an integer in the range of 1 to 12;
$R^2$ and $R^3$ are each independently H, alkyl, arylalkyl, cycloalkyl, heteroalkyl, —(CH$_2$)$_m$NHR', —(CH$_2$)$_l$CO$_2$R", —COR''' or —SO$_2$R'''', where R', R", R''' and R'''' are each alkyl, m is an integer in the range of 2 to 5, and l is an integer in the range of 1 to 5;

X and X' are each independently —O—CO—O—, —O—CO—NH—(CH$_2$)$_m$—O—, —O—CO—(CH$_2$)$_l$—O— or, —O—(CH$_2$)$_l$—CO—NH—(CH$_2$)$_m$—O—, where m and l are the same as defined above; and p is an integer in the range of 0 to 2.

9. The composition of claim 8, wherein the drug or the diagnostic reagent is an organic compound having a molecular weight ranging from 100 to 1500 g/mol.

10. The composition of claim 8, wherein the drug or the diagnostic reagent is a polymer compound selected from a peptide and a nucleic acid.

11. The composition of claim 8, wherein the inositol derivative of formula (I) forms a conjugate through a covalent bond with the drug or the diagnostic reagent.

12. The composition of claim 8, wherein the inositol derivative of formula (I) forms an ionic complex through ionic bonds with the drug or the diagnostic reagent.

* * * * *

SEQUENCE LISTING

```
<160> NUMBER OF SEQ ID NOS: 8

<210> SEQ ID NO 1
<211> LENGTH: 13
<212> TYPE: PRT
<213> ORGANISM: Artificial Sequence
<220> FEATURE:
<223> OTHER INFORMATION: a.a. 48 to 60 of HIV-1 Tat protein

<400> SEQUENCE: 1

Gly Arg Lys Lys Arg Gln Arg Arg Arg Pro Pro Gln Cys
 1               5                  10

<210> SEQ ID NO 2
<211> LENGTH: 16
<212> TYPE: PRT
<213> ORGANISM: Artificial Sequence
<220> FEATURE:
<223> OTHER INFORMATION: a.a. 43 to 58 of Antennapedia homeodomain

<400> SEQUENCE: 2

Arg Gln Ile Lys Ile Trp Phe Gln Asn Arg Arg Met Lys Trp Lys Lys
 1               5                  10                  15

<210> SEQ ID NO 3
<211> LENGTH: 34
<212> TYPE: PRT
<213> ORGANISM: Artificial Sequence
<220> FEATURE:
<223> OTHER INFORMATION: a.a. 267 to 300 of VP 22

<400> SEQUENCE: 3

Asp Ala Ala Thr Ala Thr Arg Gly Arg Ser Ala Ala Ser Arg Pro Thr
 1               5                  10                  15

Glu Arg Asp Arg Ala Pro Ala Arg Ser Ala Ser Arg Pro Arg Arg Pro
             20                  25                  30

Val Glu

<210> SEQ ID NO 4
<211> LENGTH: 8
<212> TYPE: PRT
<213> ORGANISM: Artificial Sequence
<220> FEATURE:
<223> OTHER INFORMATION: SV40 nuclear localization signal

<400> SEQUENCE: 4
```

```
Pro Lys Lys Lys Arg Lys Val Cys
1               5
```

<210> SEQ ID NO 5
<211> LENGTH: 17
<212> TYPE: PRT
<213> ORGANISM: Artificial Sequence
<220> FEATURE:
<223> OTHER INFORMATION: Nucleoplasmin nuclear localization signal

<400> SEQUENCE: 5

```
Lys Arg Pro Ala Ala Ile Lys Lys Ala Gly Gln Ala Lys Lys Lys Lys
1               5                   10                  15

Cys
```

<210> SEQ ID NO 6
<211> LENGTH: 10
<212> TYPE: PRT
<213> ORGANISM: Artificial Sequence
<220> FEATURE:
<223> OTHER INFORMATION: NF-kB

<400> SEQUENCE: 6

```
Pro Met Leu Lys Gln Arg Lys Arg Gln Ala
1               5                   10
```

<210> SEQ ID NO 7
<211> LENGTH: 17
<212> TYPE: PRT
<213> ORGANISM: Artificial Sequence
<220> FEATURE:
<223> OTHER INFORMATION: a.a. 34 to 50 of HIV-1 Rev

<400> SEQUENCE: 7

```
Arg Gln Ala Arg Arg Asn Arg Arg Arg Trp Arg Glu Arg Gln Arg
1               5                   10                  15

Gly
```

<210> SEQ ID NO 8
<211> LENGTH: 17
<212> TYPE: PRT
<213> ORGANISM: Artificial Sequence
<220> FEATURE:
<223> OTHER INFORMATION: a.a. 35 to 49 of FHV Coat

<400> SEQUENCE: 8

```
Arg Arg Arg Asn Arg Thr Arg Arg Asn Arg Arg Arg Val Arg Arg Gly
1               5                   10                  15

Cys
```